United States Patent [19]

Freedman

[11] Patent Number: 5,381,092
[45] Date of Patent: Jan. 10, 1995

[54] METHOD AND APPARATUS FOR COMPRESSING DATA PRODUCED FROM A WELL TOOL IN A WELLBORE PRIOR TO TRANSMITTING THE COMPRESSED DATA UPHOLE TO A SURFACE APPARATUS

[75] Inventor: Robert Freedman, Houston, Tex.

[73] Assignee: Schlumberger Technology Corporation, Houston, Tex.

[21] Appl. No.: 127,978

[22] Filed: Sep. 28, 1993

Related U.S. Application Data

[63] Continuation of Ser. No. 970,332, Nov. 2, 1992, Pat. No. 5,291,137.

[51] Int. Cl.$^6$ .......................................... G01R 33/20
[52] U.S. Cl. .................................................. 324/303
[58] Field of Search ............... 324/300, 307, 303, 318, 324/322; 340/855.3, 855.7, 18 CM, 858; 375/59; 367/83, 27; 341/63; 364/550

[56] References Cited

U.S. PATENT DOCUMENTS

| | | | |
|---|---|---|---|
| 4,012,712 | 3/1977 | Nelligan | 340/18 CM |
| 4,216,536 | 8/1980 | More | 367/83 |
| 4,355,310 | 10/1982 | Belaigues et al. | 340/858 |
| 4,495,639 | 1/1985 | Mosier et al. | 341/63 |
| 4,531,189 | 7/1985 | Mosier et al. | 364/550 |
| 4,626,824 | 12/1986 | Larson | 341/95 |
| 4,985,873 | 1/1991 | Eyl et al. | 367/27 |
| 5,010,333 | 4/1991 | Gardner et al. | 340/855.3 |
| 5,031,155 | 7/1991 | Hsu | 367/25 |
| 5,253,271 | 10/1993 | Montgomery | 375/59 |
| 5,291,137 | 3/1994 | Freedman | 324/303 |

OTHER PUBLICATIONS

A book entitled "Vector Quantization and Signal Compression", by Allen Gersho & Robert M. Gray, Kluwer Academic Publishers, copyright 1992, pp. vii–xi, xiii–xxi, and 1–13.
An article entitled "Wave Separation and Feature Extraction of Acoustic Well-logging Waveforms using Karhunen-Loeve Transformation", Geophysics, vol. 55, No. 2, Feb. 1990, pp. 176–184.
An article entitled "Transform Methods for Seismic Data Compression", IEEE Transactions on Geoscience and Remote Sensing, vol. 29, No. 3, May 1991, pp. 407–416.
An article entitled "Statistical Method for the Determination of Zone Boundaries Using Well Log Data", SPE 14470, 1985, Society of Petroleum Engineers, by H. P. K. Dharmawardhana, and G. V. Keller.
An article entitled "Integral Transforms, Data Compression, and Automatic Analysis of Seismic Sections", by Richard A. Strelitz and Yehoshua Keshet, IEEE Transactions on Geoscience and Remote Sensing, vol. 28, No. 6, Nov. 1990.
A meeting paper entitled "Optimized Drilling-Closing the Loop", by R. L. Monti, J. S. Hushital, and T. M. Burgess, 12th World Petroleum Congress (Houston Apr. 26, 1987 to May 1, 1987) Proc V 3, pp. 131–142, 1987.

*Primary Examiner*—Michael J. Tokar
*Attorney, Agent, or Firm*—Henry N. Garrana; John H. Bouchard

[57] ABSTRACT

A wellbore apparatus adapted to be disposed in a wellbore is electrically connected to a surface apparatus disposed at a surface of the wellbore. When disposed in the wellbore, the wellbore apparatus receives a plurality of input signals from an earth formation traversed by the wellbore which are representative of characteristics of the earth formation. The wellbore apparatus includes a data compression apparatus which receives the input signals and compresses the input signals prior to transmission of the compressed input signals uphole to the surface apparatus. The data compression apparatus compresses the input signals by first subdividing the plurality of input signals into a plurality of groups, where the number of the plurality of groups is much less than the number of the plurality of input signals, and then generating one value for each group. Therefore, a plurality of values corresponding, respectively, to the plurality of groups represent the compressed input signals transmitted uphole to the surface apparatus. In addition, since the plurality of values is much less in number than the plurality of input signals, the telemetry requirements needed to transmit the plurality of values uphole, relative to the telemetry requirements needed to transmit the plurality of input signals uphole, is substantially reduced.

51 Claims, 17 Drawing Sheets

$B_0 = 0$ (WITHOUT
$M \cong 0$ MAGNET)

$B_0 \neq 0$ (WITH
$M \neq 0$ MAGNET)

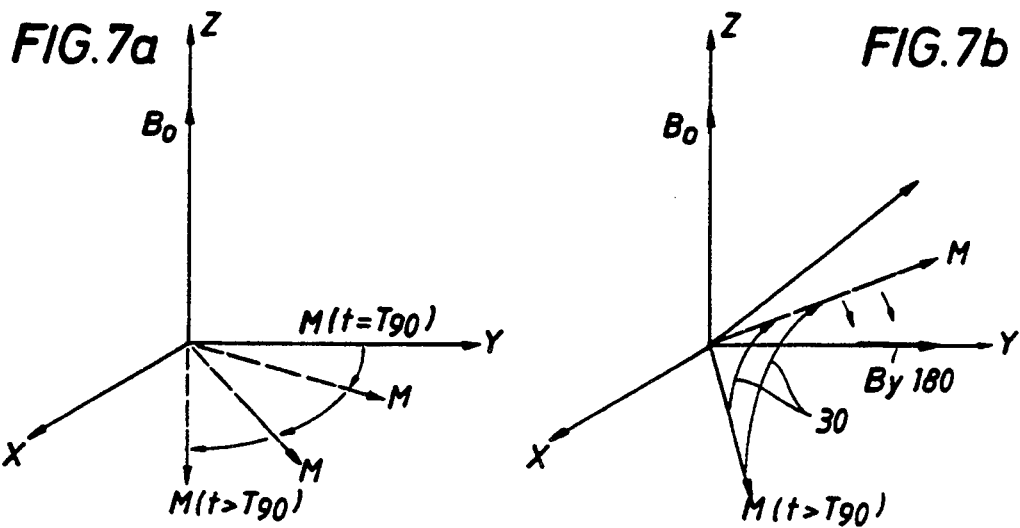
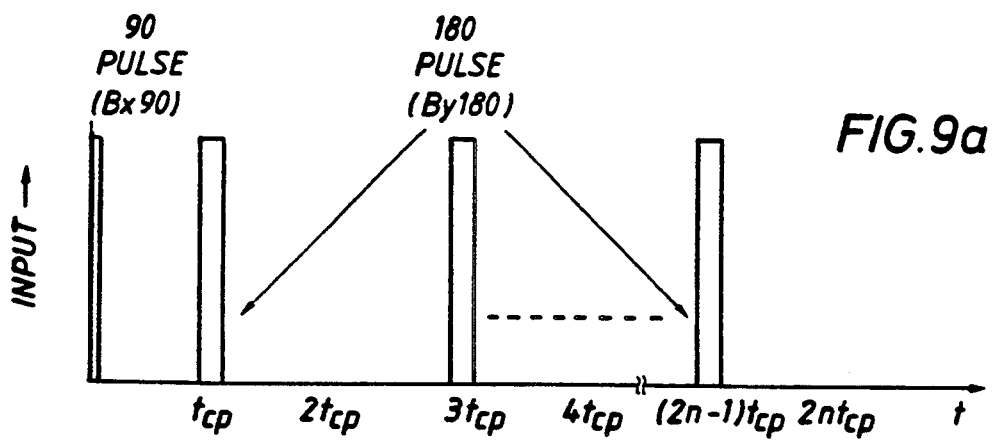
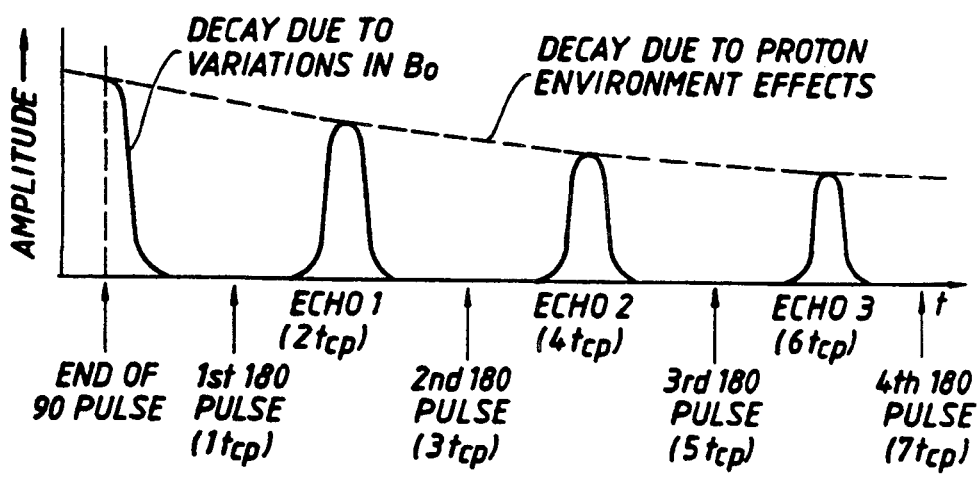

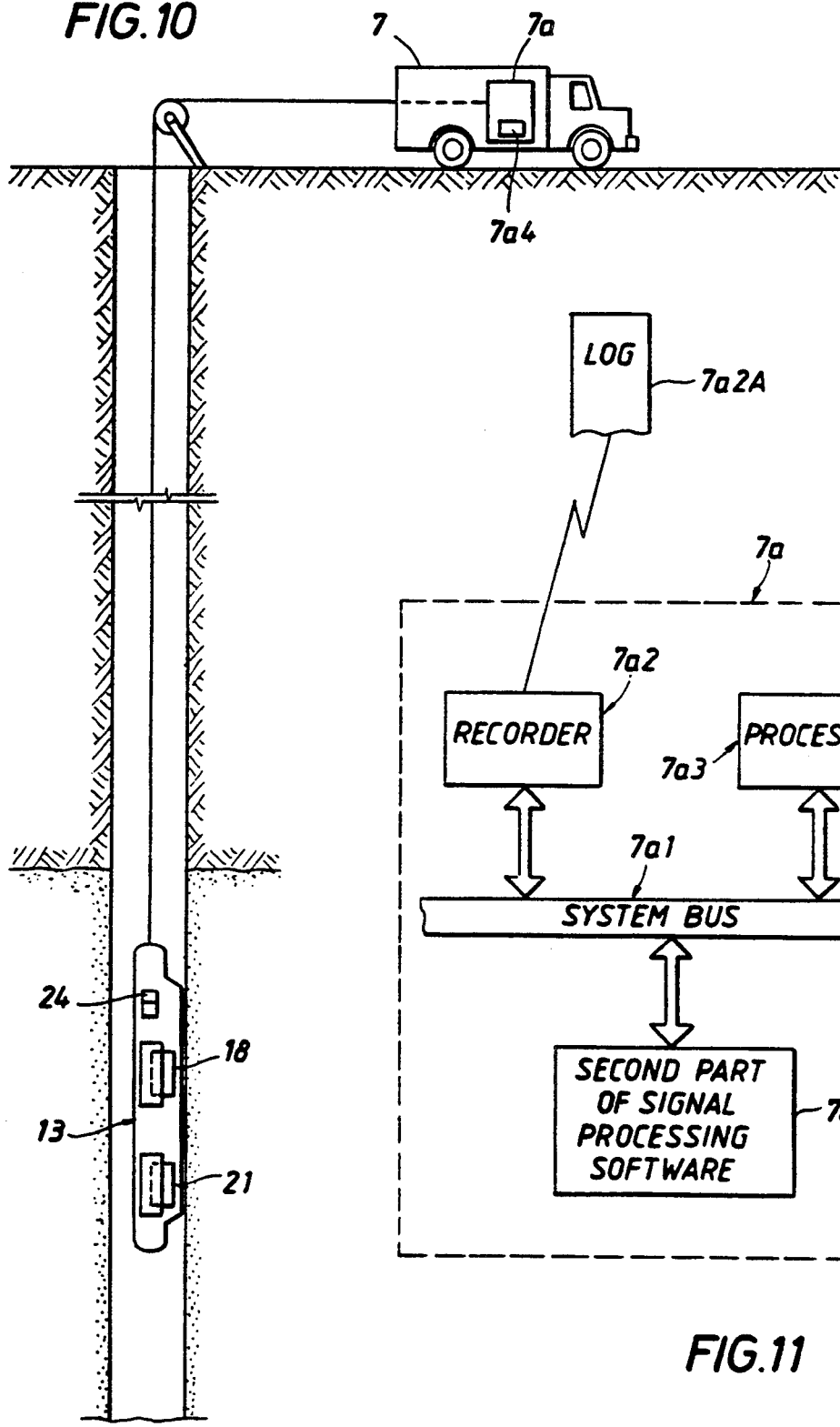

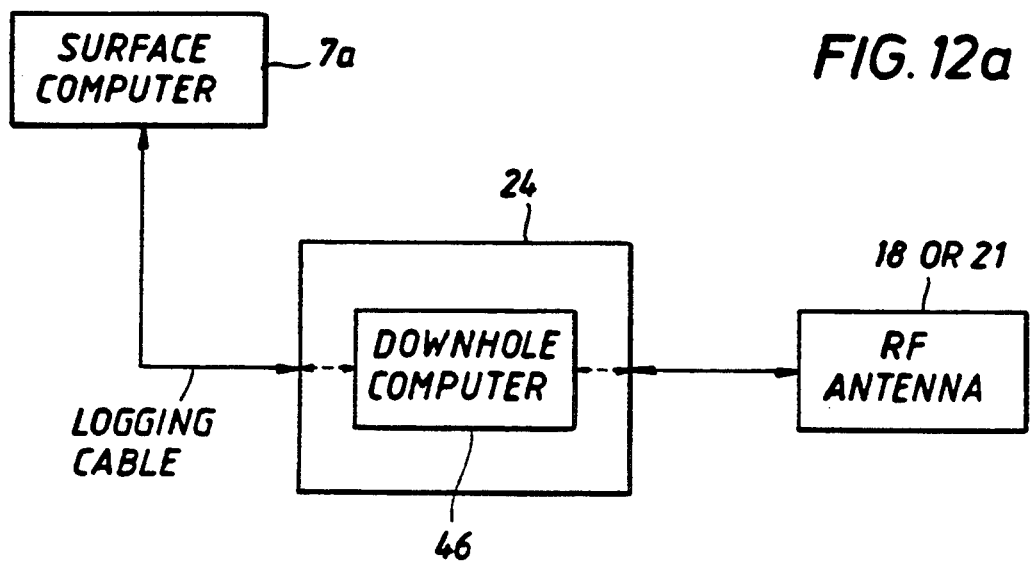
FIG.12a
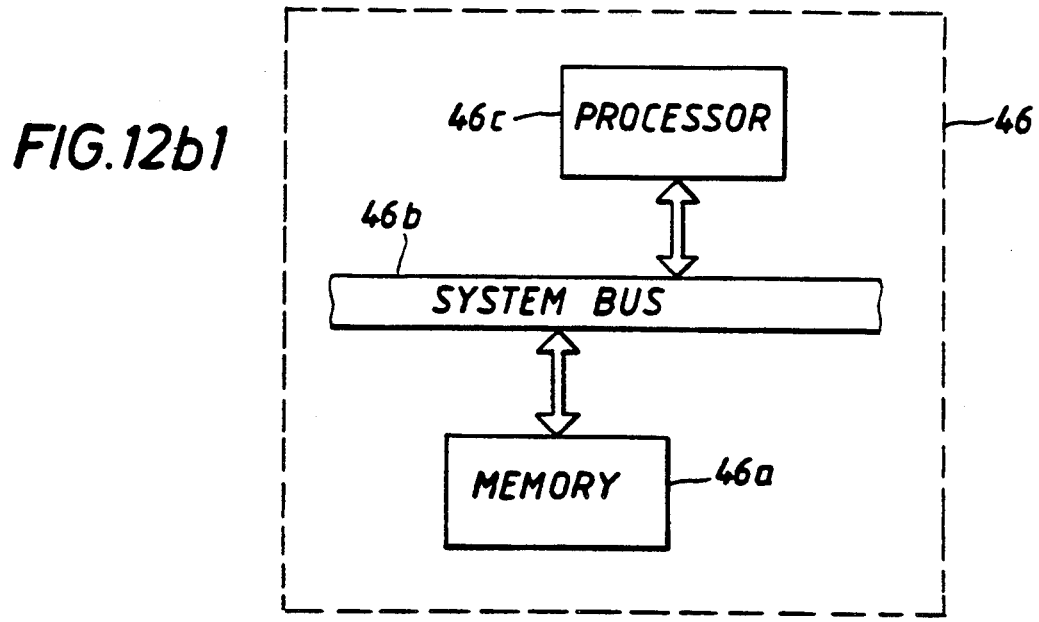
FIG.12b1
FIG.12b2

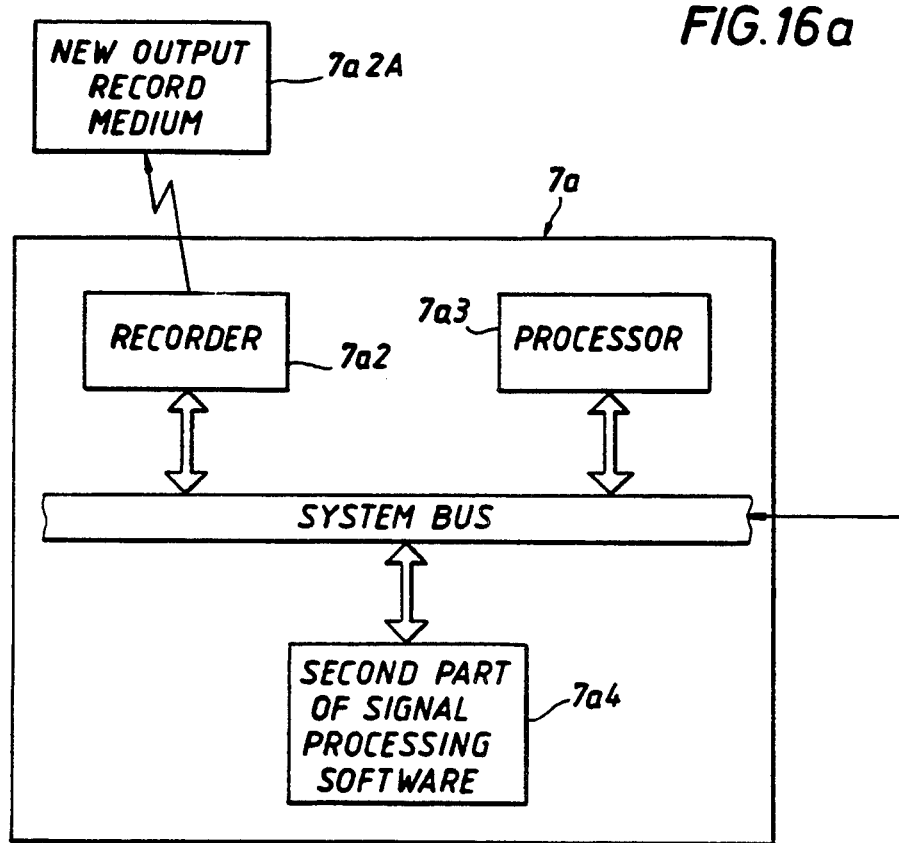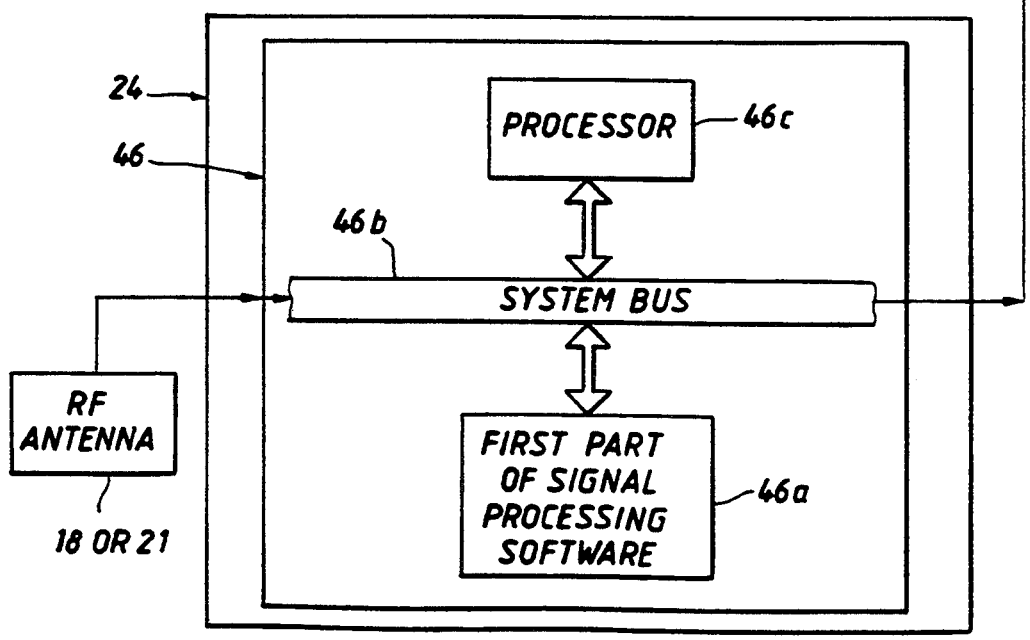
FIG.16a

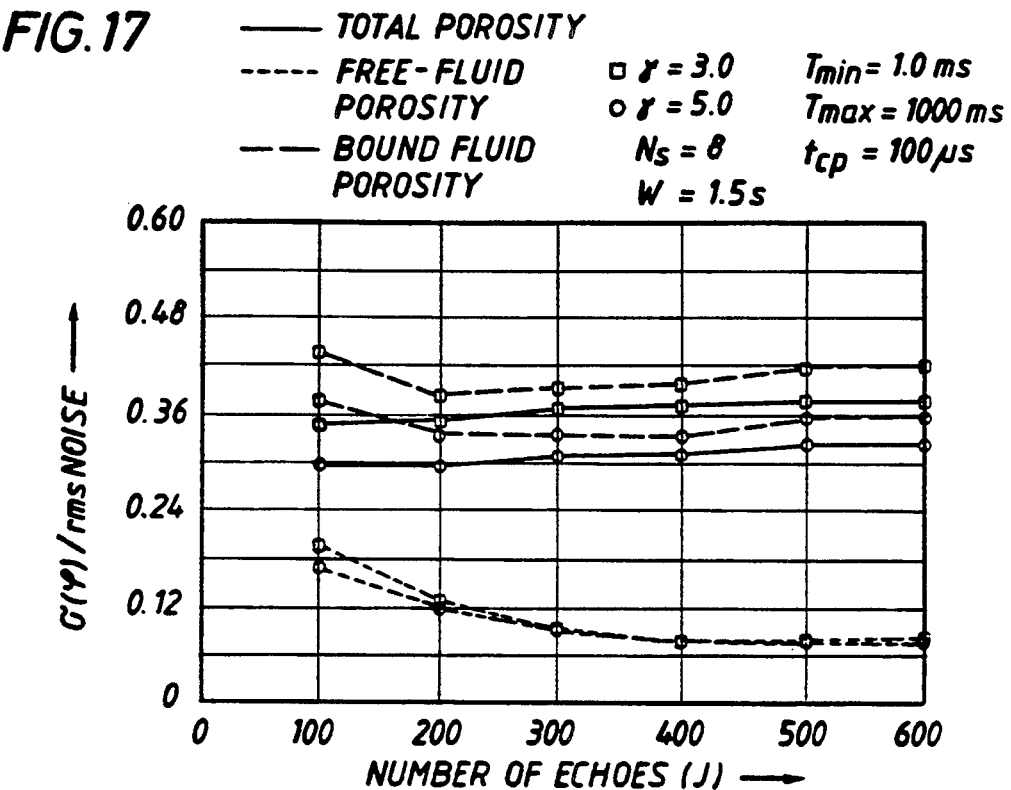
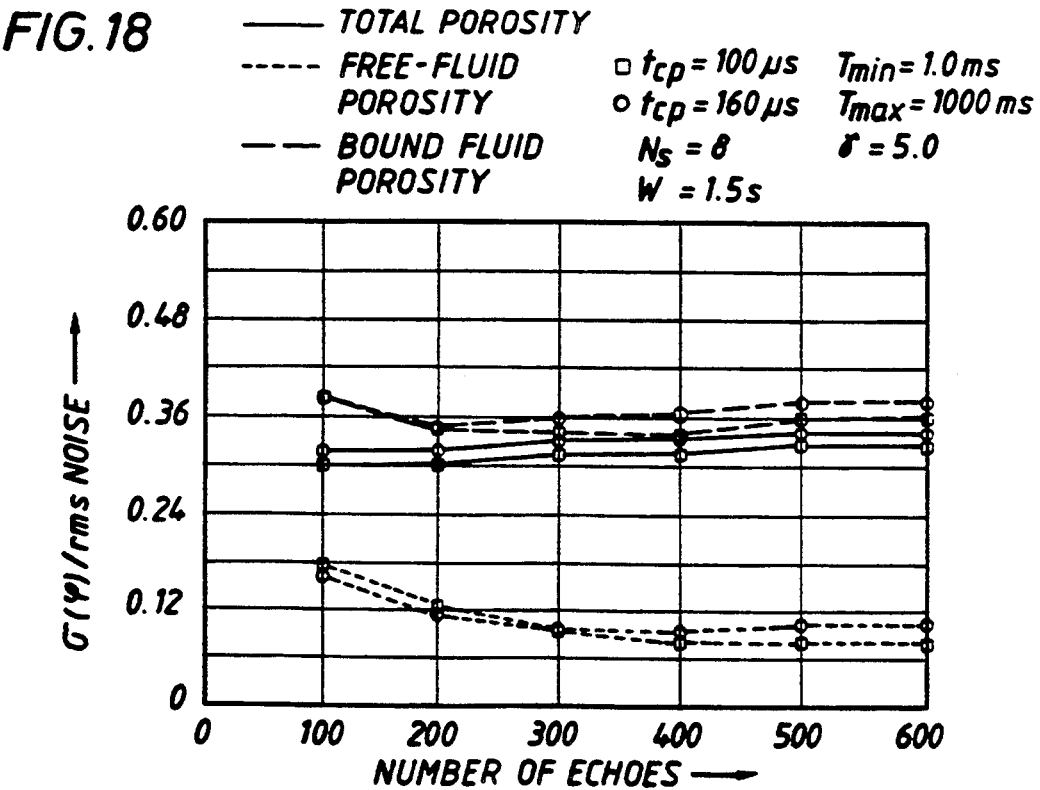

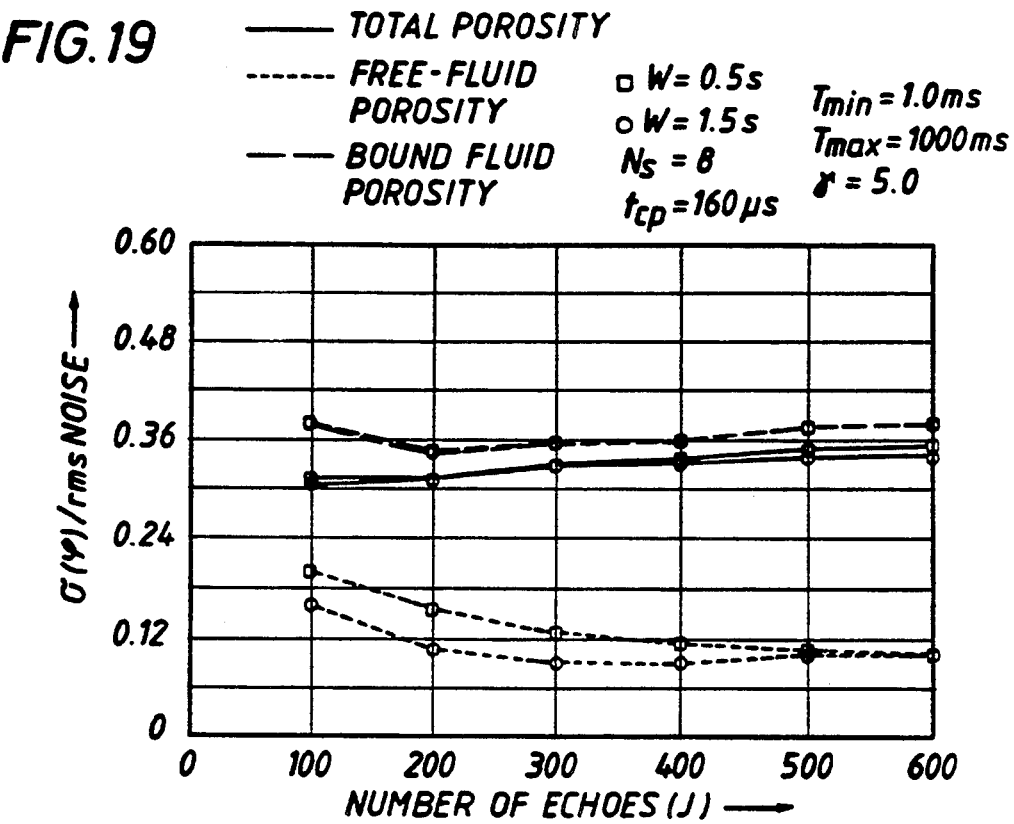
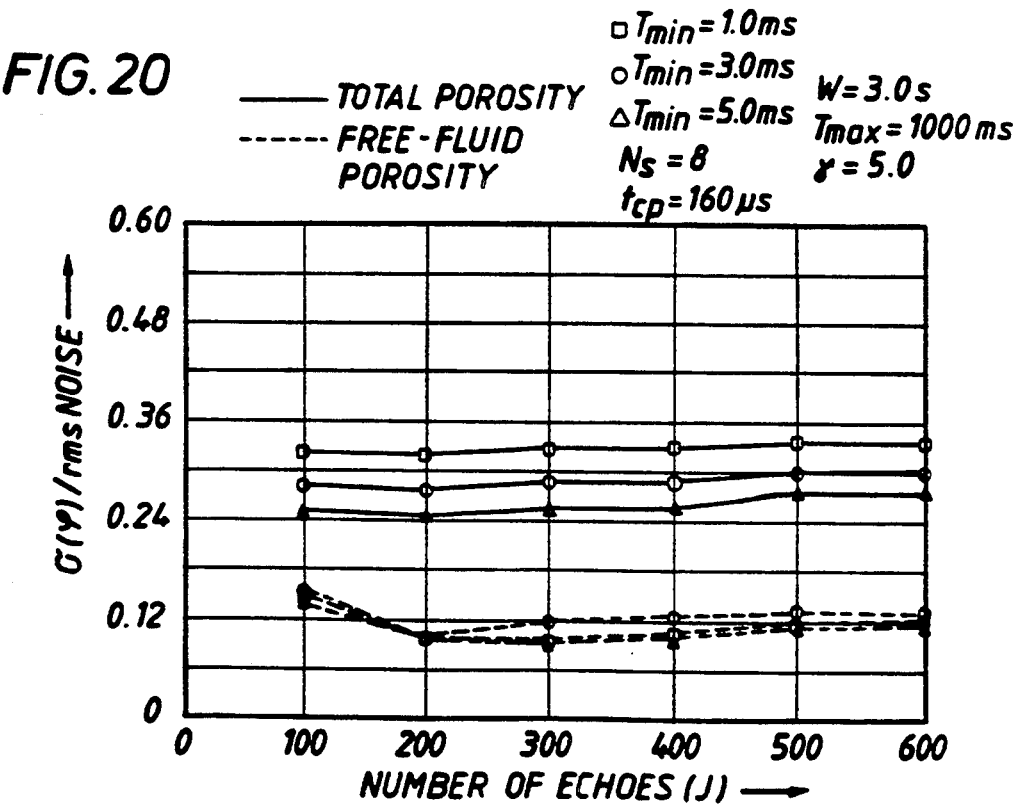

METHOD AND APPARATUS FOR COMPRESSING DATA PRODUCED FROM A WELL TOOL IN A WELLBORE PRIOR TO TRANSMITTING THE COMPRESSED DATA UPHOLE TO A SURFACE APPARATUS

This is a continuation of application Ser. No. 07/970,332 filed Nov. 2, 1992 U.S. Pat. No. 5,291,137.

BACKGROUND OF THE INVENTION

The subject matter of the present invention relates to a new method and apparatus for processing a signal which is output from a pulsed nuclear magnetism tool disposed in a wellbore thereby producing new output data representative of the formation traversed by the wellbore and for recording the new output data on an output record medium.

Repeated attempts have been made to use the principles of nuclear magnetic resonance by means of logging tools lowered through wellbores in oil exploration over the past several decades. It is recognized that particles of a formation having magnetic spin, for example atomic nuclei, protons, or electrons, have tendencies to align with a magnetic field which is imposed on the formation. Such a magnetic field may be naturally generated, as is the case with the earth's magnetic field ($B_E$) which has an intensity of approximately 0.5 gauss in areas of the globe where boreholes are typically drilled. Any given particle in a formation is additionally influenced by localized magnetic fields associated with nearby magnetic particles, other paramagnetic materials, and the layer of ions which typically line pore walls of certain types of formations such as shales. These localized fields tend to be inhomogeneous, while the earth's magnetic field is relatively homogeneous.

A nuclear magnetic resonance (NMR) logging tool apparatus, adapted to be disposed in a borehole, produces a static and a substantially homogeneous magnetic field focussed into a formation on one side of the logging tool. By directing and configuring the combined magnetic fields of a plurality of magnets, a region, remote from the plurality of magnets, is introduced wherein the spacial field gradient substantially vanishes, thereby insuring that the field is highly homogeneous throughout that region. In a preferred form, the magnets are mounted within a metallic skid or logging pad, the static magnetic field is directed through the face of the pad into an adjacent formation, and the region of substantially homogeneous field is situated in a volume of formation behind the mudcake layer which typically lines borehole walls. A homogeneous magnetic field, several hundred times stronger than the earth's magnetic field, can be thus imposed, or "focused", on a volume of formation in situ.

Reference may be had to U.S. Pat. No. 4,933,638 issued Jun. 12, 1990 to Kenyon et al (hereinafter termed, the "Kenyon et al patent" or "Kenyon et al") for details of such a nuclear magnetic resonance (NMR) logging tool apparatus, which patent is incorporated herein by reference. In the Kenyon et al patent, an RF antenna is mounted on the outside of the structure of the pad so that the pad serves as a natural shield against any signals which may be generated by resonant conditions behind the pad, particularly those potentially strong resonance signals from borehole fluid. In the preferred form, the antenna is configured to focus its signals radially outwardly from the pad face, into the volume of formation having the homogeneous field, thereby additionally reducing the distortion of measured signals from borehole effects.

All such nuclear magnetic resonance logging tool apparatus, when disposed in a borehole, are electrically connected to a computing apparatus disposed at the surface of the borehole. The computing apparatus stores a signal processing software therein, the software in conjunction with the hardware of the computing apparatus producing a plurality output data representative of the characteristics of the formation traversed by the borehole when the software is executed by the hardware while utilizing a set of input data which was developed by the logging tool disposed in the borehole.

While the prior art nuclear magnetic resonance logging tool of Kenyon et al, and its associated signal processing software, is capable of determining formation characteristics with sufficient accuracy and dependability, it has been found useful to improve the performance and accuracy of such logging tool, especially in view of the inherent difficulties of making nuclear magnetic resonance (NMR) measurements in boreholes.

One very important improvement in the performance of the Kenyon et al logging tool can be made to the signal processing software used by Kenyon et al. Several approaches to spectral decomposition or signal processing of NMR data have been reported. Spectral decomposition is a signal processing method that determines from NMR spin-echo signals in rocks, the individual amplitude components of the multi-exponential signal. These individual components correspond to different pore sizes in the rock.

A first approach is reported by Kenyon, W. E., Howard, J. J., Sezginer, A. Straley, C., Matteson, A., Horkowitz, R., and Erlich, R., in an article entitled "Poresize Distribution and NMR in Microporous Cherty Sandstones", Trans of the SPWLA of the 30th Ann. Logging Symp., Paper LL, Jun. 11–14, 1989, this first approach being further set forth in an article entitled "A NMR Technique for the Analysis of Pore Structure: Determination of Continuous Pore Size Distributions"; Gallegos, D. P. and Smith, D. M.; J. of Colloid and Interface Science, V. 122, no. 1, pp. 143–153, March 1988, the disclosures of which are incorporated by reference into this specification.

A second approach is set forth in an article entitled "Problems in Identifying Multimodal Distributions of Relaxation Times for NMR in Porous Media", Magnetic Resonance Imaging, Vol 9, pp. 687–693 (1991), the disclosure of which is incorporated by reference into this specification.

The aforementioned approaches are computationally too intensive to be done in real time by a logging truck computer. They also do not compress the data which is needed to limit the telemetry requirements for sending data uphole. In addition, the NMR logging tool should first acquire downhole spin-echo measurements in earth formations penetrated by a borehole and then, secondly, generate a set of detailed formation evaluation information. However, this type of detailed formation evaluation information was previously obtainable only from costly laboratory analysis of conventional core data. Therefore, a signal processing method and apparatus is needed which is adapted to extract this formation evaluation information from the measured spin-echos. This signal processing method and apparatus must be capable of providing a spectral decomposition of the measured data, and it must be efficient and robust for real time processing of measured data during the acquisition of the data by an NMR logging tool moving in the borehole. Moreover, it is desirable to compress the data by elimination of redundant information. This reduces the telemetry requirements of the NMR tool, which is important if the tool is run in combination with other logging tools.

SUMMARY OF THE INVENTION

Accordingly, it is a primary object of the present invention to provide a new signal processing method and apparatus which is capable of extracting a new set of specific formation evaluation information from measured spin-echo data acquired from a nuclear magnetic resonance (NMR) logging tool which is disposed in a borehole and moves within such borehole.

It is a further object of the present invention to provide a new signal processing method and apparatus responsive to measured spin echo data for providing a spectral decomposition of the measured spin-echo data and subsequently generating a new set of specific formation evaluation information from the spectral decomposition, the signal processing method being efficient, flexible and robust for real time processing of the measured spin echo data during the acquisition of such data by a NMR logging tool moving axially within the borehole.

It is a further object of the present invention to provide a new signal processing method and apparatus responsive to a set of measured spin echo data for extracting specific formation evaluation information from the measured spin echo data acquired from a NMR logging disposed in a borehole, the signal processing method and apparatus including a first part stored downhole in a downhole microcomputer for compressing and eliminating redundant information from the set of measured spin echo data and generating a plurality of window sums, where the number of the plurality of window sums is much less than the number of the set of measured spin echo data, the plurality of window sums being transmitted uphole, and a second part stored uphole in a surface oriented computer system and responsive to the plurality of window sums received from the downhole microcomputer for generating a new set of specific formation evaluation information representative of characteristics of a formation traversed by the borehole.

It is a further object of the present invention to provide the new signal processing method and apparatus which generates the new set of specific formation evaluation information representative of characteristics of the formation traversed by the borehole, which new set of specific formation evaluation information includes total NMR porosity, free fluid porosity, bound fluid porosity, spin-spin (T2) relaxation time distributions which are related to pore size distributions in the formation, and continuous permeability logs.

It is a further object of the present invention to provide the new signal processing method and apparatus which generates the new set of specific formation evaluation information, which specific formation evaluation information includes the following information: total NMR porosity, free fluid porosity, porosity standard deviation, free fluid standard deviation, and measurement diagnostics including RMS noise estimate and signal phase.

It is a further object of the present invention to provide the new signal processing method and apparatus which provides the aforementioned new set of specific formation evaluation information and which generates a new output record medium illustrating the specific formation evaluation information, the new output record medium comprising a plurality of logs, each log illustrating a particular one of the aforementioned set of specific formation evaluation information and measurement diagnostics as a function of depth in the borehole.

In accordance with these and other objects of the present invention, a nuclear magnetic resonance (NMR) logging system includes: (1) a NMR logging tool adapted to be disposed in a borehole, the logging tool including a downhole microcomputer; (2) a processing system adapted to be disposed at the surface of the borehole and electrically connected to the logging tool for processing signals received from the logging tool, the processing system including a computer having a memory; and (3) a signal processing method and apparatus embodied in the form of a software package having a first part stored downhole in the downhole microcomputer of the logging tool for compressing and eliminating redundant information from received and measured spin echo data and generating compressed information; and a second part stored uphole in the surface oriented computer of the processing system and responsive to the compressed information for generating the new set of specific formation evaluation information and for further generating an output record medium which illustrates the specific formation evaluation information.

In the logging tool disposed in the borehole, a receiving antenna measures voltages induced by the precession of the magnetic moments of individual protons in the volumes of the formation traversed by the borehole and generates a plurality of spin-echo receiver voltage pulses representative of the magnetic moments. An electronics cartridge, which includes a microcomputer, begins processing the receiver voltage pulses by integrating each of the spin-echo receiver voltage pulses over a time interval, there being a total of J time intervals, each time interval being centered about a time $t_j = j$ delta, where $j=1, 2, \ldots, J$. The integrated signals are recorded as spin-echo inphase ($\tilde{R}_j$) and quadrature ($\tilde{X}_j$) amplitudes, time series channels or waveforms. In the DESCRIPTION OF THE PREFERRED EMBODIMENT, the symbols "$R_j$" and "$X_j$" will be written without a "tilde symbol overbar", whereas the same symbols in the DETAILED DESCRIPTION will be written with the tilde symbol overbar.

In the microcomputer, using the first part of the signal processing method and apparatus in accordance with the present invention, a signal phase (theta) is estimated from the 2J spin-echo in-phase ($R_j$) and quadrature ($X_j$) amplitudes associated with the 2J spin-echo receiver voltage pulses. Then, the in-phase ($R_j$) amplitude, quadrature ($X_j$) amplitude, and the signal phase (theta) associated with each of the spin-echo receiver voltage pulses are combined to produce a signal plus noise amplitude $A_j^{(+)}$. A plurality of the signal plus noise amplitudes $A_j^{(+)}$ are disposed within a time window, there being a plurality of time windows. A sum of the plurality of signal plus noise amplitudes $A_j^{(+)}$ within each time window produces a window sum $I_{m,m+1}$; and, since there are a plurality of time windows, there are a plurality of window sums $I_{m,m+1}$. Consequently, the downhole microcomputer of the NMR logging tool disposed in the borehole generates a plurality of the window sums $I_{m,m+1}$, one for each time window, and transmits the plurality of the window sums uphole to the processing system located at the surface of the borehole. Note that each window sum $I_{m,m+1}$ itself represents a reduced set of data, since each window sum $I_{m,m+1}$ is the sum of a plurality of signal plus noise amplitudes $A_j^{(+)}$. As a result, the telemetry requirements needed by the logging tool to transmit the plurality of window sums $I_{m,m+1}$ uphole to the processing system located at the wellbore surface are substantially reduced. In addition to producing the signal plus noise amplitude $A_j^{(+)}$, the downhole microcomputer also produces a set of "J" amplitudes $A_j^{(-)}$. These amplitudes $A_j^{(-)}$ are used by the downhole microcomputer for estimating an RMS noise, which is defined to be the square root of "psi", where "psi" is the noise power. The RMS noise is also transmitted uphole to the processing system disposed at the wellbore surface.

In the processing system disposed at the wellbore surface, using the second part of the signal processing method and apparatus in accordance with the present invention, the RMS noise is used to compute three standard deviations: the standard deviation "sigma(phi$_{nmr}$)", the standard deviation "sigma(phi$_f$)", and the standard deviation "sigma(T$_{2,log}$)". These standard deviations are used to generate the new output record medium in accordance with the present invention. The RMS noise is also used to compute the dimensionless parameter "gamma", the use of which is discussed below. As noted earlier, the plurality $N_w$ of the window sums $I_{m,m+1}$ are transmitted uphole by the downhole computer. The processing system located at the wellbore surface includes a surface computer. The surface computer receives the plurality $N_w$ of the window sums $I_{m,m+1}$; and, using the plurality $N_w$ of window sums $I_{m,m+1}$ and the aforementioned dimensionless parameter "gamma", the surface computer determines a logarithm of the likelihood function $(-\ln L)$ for the $N_w$ window sums set forth in equation 42 in the detailed description of the preferred embodiment. The logarithm of the likelihood function $(-\ln L)$ of equation 42 is a function of a set of spectral amplitudes "$a_1$", where such spectral amplitudes are determined by minimization of equation 42. The spectral amplitudes "$a_1$" are used by the surface computer: (1) to compute three log outputs, phi$_{nmr}$, phi$_f$, and T$_{2,log}$, and (2) to compute signal distributions P$_a$(logT$_2$) which are represented by color maps.

The new output record medium in accordance with the present invention is generated using the three log outputs, the signal distributions for color maps, and the three standard deviations.

Further scope of applicability of the present invention will become apparent from the detailed description presented hereinafter. It should be understood, however, that the detailed description and the specific examples, while representing a preferred embodiment of the present invention, are given by way of illustration only, since various changes and modifications within the spirit and scope of the invention will become obvious to one skilled in the art from a reading of the following detailed description.

BRIEF DESCRIPTION OF THE DRAWINGS

A full understanding of the present invention will be obtained from the detailed description of the preferred embodiment presented hereinbelow, and the accompanying drawings, which are given by way of illustration only and are not intended to be limitative of the present invention, and wherein:

FIGS. 7a–7b illustrate the precession of the individual magnetic moments vector m1 and the effects on this magnetic moments vector m1 of the presence of two other magnetic fields: the static magnetic field B0 and a radio frequency magnetic field By$_{180}$, the direction of which is transverse to the magnetic field B0 and is directed along the y-axis;

FIGS. 9a–9b illustrate the spin-echo transmitter and receiver voltage pulses produced by the logging tool in time relation to: (1) a first magnetic field pulse which is directed along the x-axis of FIG. 6 and has a pulse duration of T90 (the first magnetic field pulse being hereinafter termed "B$_{x90}$" or "the 90 pulse"), and (2) a second magnetic field pulse directed along the y-axis and having a pulse duration of T180 which rotates all of the proton spins 180 degrees about the y-axis (the second magnetic field pulse being hereinafter termed B$_{y180}$);

FIG. 10 illustrates NMR logging tool disposed in a borehole including an electronics cartridge which stores the first part of the signal processing method and apparatus in accordance with the present invention, and the processing system disposed on the surface of the borehole which stores the second part of the signal processing method and apparatus in accordance with the present invention;

FIG. 11 illustrates a more detailed construction of the surface oriented processing system of FIG. 10 which stores the second part of the signal processing method and apparatus of the present invention;

FIGS. 12a, 12b1 and 12b2 illustrate a more detailed construction of the electronics cartridge of FIG. 10 which stores the first part of the signal processing method and apparatus of the present invention;

FIG. 16a illustrates a more detailed block diagram of the surface computer and the downhole computer of FIG. 12a utilized in conjunction with FIG. 13 for providing a functional description of the present invention;

FIG. 17 illustrates the standard deviation in porosity estimates versus the total number of echos for two values of "gamma";

FIG. 18 illustrates the standard deviation in porosity estimates versus the total number of echos for two values of $t_{cp}$;

FIG. 19 illustrates the standard deviation in porosity estimates versus the total number of echos for two values of W:

FIG. 20 illustrates the standard deviation in porosity estimates versus the total number of echos for three values of $T_{min}$;

DESCRIPTION OF THE PREFERRED EMBODIMENT

This specification is divided into two parts:

(1) a Description of the Preferred Embodiment, which provides a general, more understandable description of the new signal processing method and apparatus of the present invention; and (2) a Detailed Description of the Preferred Embodiment, which provides a more detailed description of the new signal processing method and apparatus of the present invention.

Figure 1:
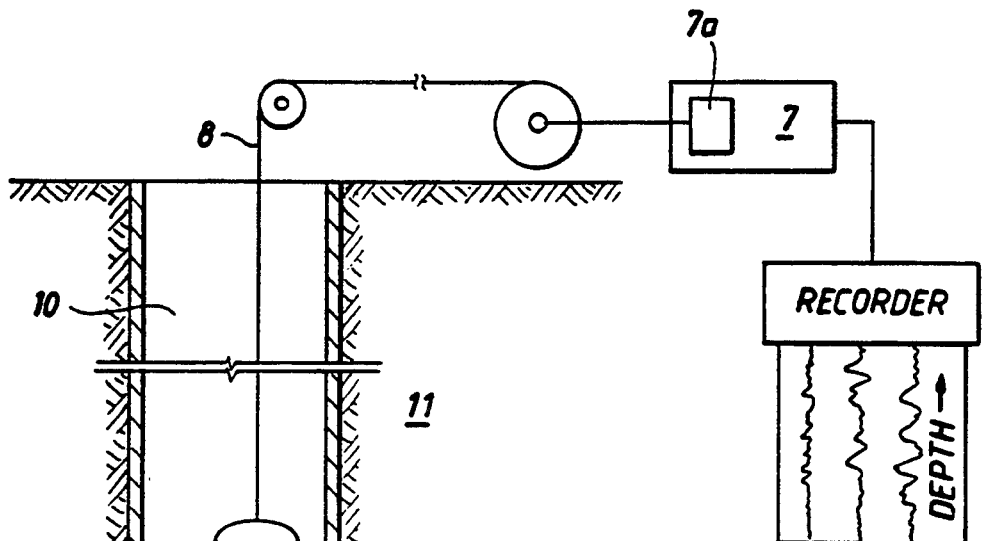
FIG. 1 illustrates a nuclear magnetic resonance (NMR) logging system including a NMR logging tool disposed in a wellbore and a processing system disposed at the wellbore surface for processing signals transmitted uphole by the logging tool.

Referring to FIG. 1, a nuclear magnetic resonance (NMR) logging system is illustrated, the NMR logging system including a NMR logging tool 13 disposed in a wellbore and a processing system 7a disposed at the wellbore surface for processing signals transmitted uphole by the logging tool.

In FIG. 1, a borehole 10 is shown adjacent to formations 11, 12, the characteristics of which are to be determined. Within borehole 10 there is shown a logging tool 13 connected via a wireline 8 to surface equipment 7. The surface equipment 7 includes a processing system 7a which stores therein a signal processing method and apparatus embodied in the form of software. The processing system 7a will be discussed in more detail with reference to FIGS. 12 and 13 of the drawings. Tool 13 preferably has a face 14 shaped to intimately contact the borehole wall, with minimal gaps or standoff. The tool 13 also has a retractable arm 15 which can be activated to press the body of the tool 13 against the borehole wall during a logging run, with the face 14 pressed against the wall's surface. Although tool 13 is shown in the preferred embodiment of FIG. 1 as a single body, the tool may obviously comprise separated components such as a cartridge, sonde or skid, and the tool may be combinable with other logging tools as would be obvious to those skilled in the art. Similarly, although wireline 8 is the preferred form of physical support and communicating link for the invention, alternatives are clearly possible, and the invention can be incorporated in a drill stem, for example, using forms of telemetry which may not require a wireline. The formations 11, 12 have distinct characteristics such as formation type, porosity, permeability and oil content, which can be determined from measurements taken by the tool. Deposited upon the borehole wall of formations 11, 12 is typically a layer of mudcake 16 which is deposited thereon by the natural infiltration of borehole fluid filtrate into the formations. In the preferred embodiment shown in FIG. 1, tool 13 comprises a first set magnet array 17 and an antenna 18 positioned between the array 17 and the wall engaging face 14. Magnet array 17 produces a static magnetic field B0 in all regions surrounding the tool 13. The antenna 18 produces, at selected times, an oscillating radio frequency magnetic field B1 (previously denoted as "$B_{x90}$" and "$B_{y180}$") which is focussed into formation 12, and is superposed on the static field B0 within those parts of formation opposite the face 14. The field B1 is perpendicular to the field B0. The Volume of Investigation, 19, of the tool for the first set magnet array 17 shown in dotted lines FIG. 1, is a vertically elongated region directly in front of tool face 14 in which the magnetic field produced by the magnet array 17 is substantially homogeneous and the spatial gradient thereof is approximately zero. The tool 13 may also comprise, as an option, a second set magnet array 20 and an antenna 21 positioned between the array 20 and the wall engaging face 14. Magnet array 20 produces another static magnetic field B0 in all regions surrounding the tool 13. The antenna 21 produces, at selected times, an oscillating radio frequency magnetic field B1 which is again focussed into formation 12, and is superposed on the static field B0 within those parts of formation opposite the face 14. The Volume of Investigation 22 of the tool for the second set magnet array 20, shown in dotted lines in FIG. 1, is a vertically elongated region directly in front of tool face 14 in which the magnetic field produced by the magnet array 20 is substantially homogeneous and the spatial gradient thereof is approximately zero. Due to the particular magnet arrangement for the second set magnet array 20, the Volume of Investigation 22 is at a depth in the formation 12 which is greater than the depth at which the Volume of Investigation 19 is located. A prepolarizing magnet 23, shown in dotted lines, may be positioned directly above the array 17 in a modified embodiment of the invention in accordance with the teachings of the aforementioned Kenyon, et al patent. An electronics cartridge 24 is positioned above the magnet 23. The electronics cartridge 24 includes a downhole microcomputer. The electronics cartridge 24, including the downhole microcomputer, will be discussed in more detail with reference to FIGS. 12a–12b of the drawings.

In operation, referring to FIG. 1, the tool 13 makes a measurement in the Volume of Investigation 19 by magnetically reorienting the nuclear spins of particles in formation 12 with a pulse of oscillating magnetic field B1 (previously denoted as "$B_{x90}$" and "$B_{y180}$"), and then detecting the precession of the tipped particles in the static, homogeneous field B0 within the Volume of Investigation 19, over a period of time. As seen in FIG. 1, this Volume of Investigation does not overlap the surface of the wall engaging face 14 as in some previous logging tools, and does not overlap the mudcake 16 on the borehole wall. In a pulse echo type of measurement, a pulse of RF current is passed through the antenna 18 to generate a pulse of RF field B1 where the RF frequency is selected to resonate only hydrogen nuclei subjected to a static magnetic field strength equal or nearly equal to the field B0 within the Volume of Investigation 19. The signals induced in antenna 18 subsequent to the RF pulse B1 represent a measurement of nuclear magnetic precession and decay within the Volume, automatically excluding any undesirable contributions from the borehole fluid, mudcake, or surrounding formations where the field strength of B0 is substantially different. The tool 13 makes a measurement in the Volume of Investigation 22 in the same manner discussed above with respect to the Volume of Investigation 19 but utilizing the second set magnet array 20 and the antenna 21.

The general principles associated with nuclear magnetic resonance well logging, utilized by the NMR logging system of FIG. 1, will be discussed in the following paragraphs with reference to FIGS. 2 through 10 of the drawings.

Figure 2:
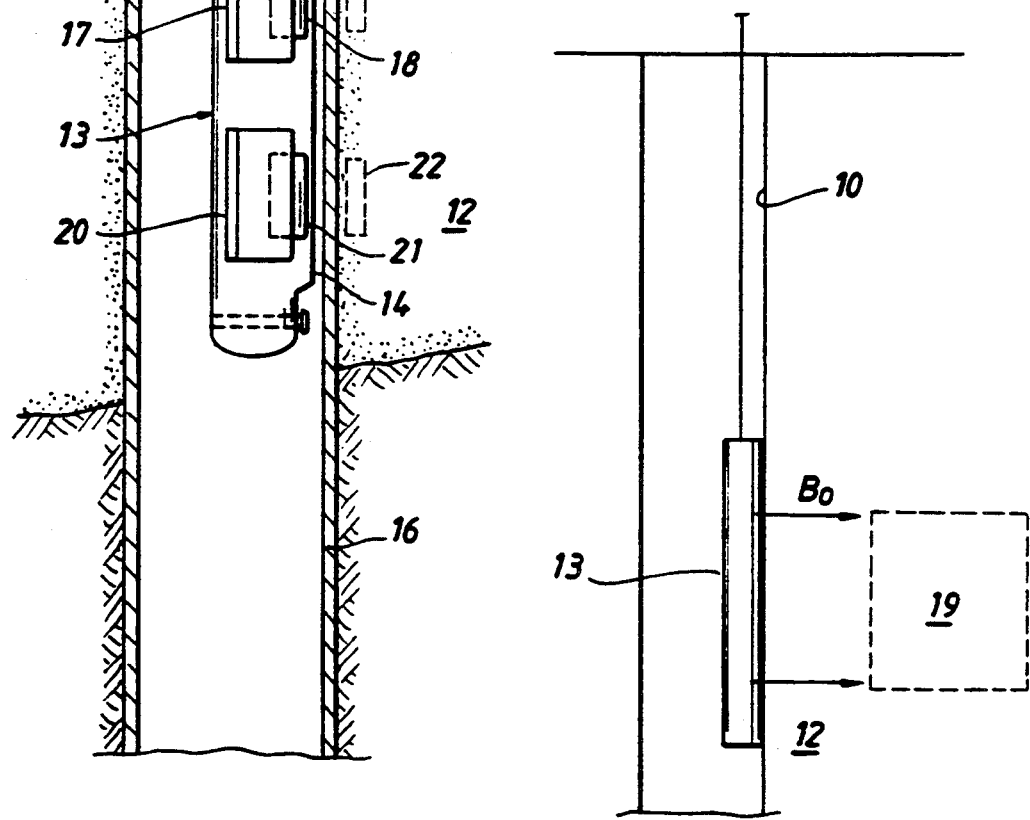
FIG. 2 illustrates a sketch of the logging tool in the wellbore producing a static magnetic field B0 into a formation traversed by the wellbore.

In FIG. 2, a NMR tool 13 contacts a wall of the borehole 10. A magnet disposed within the tool 13 generates a static magnetic field B0, which field B0 is directed toward a volume of investigation 19 disposed within a portion of the formation 12 traversed by the borehole 10.

Figure 3:
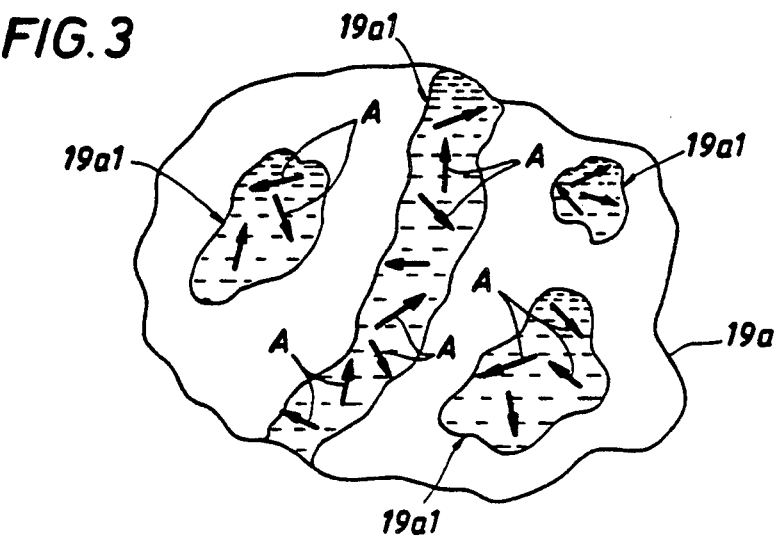
FIGS. 3–5 illustrate sections of the formation adjacent the logging tool in the wellbore and the effects of the magnetic field B0 on the composite magnetic moment vector M representative of the sum of a plurality of individual magnetic moments associated with a corresponding plurality of protons disposed within elements of the formation.

FIG. 3 illustrates a cross section 19a of the volume of investigation 19 of FIG. 2. The cross section 19a includes a plurality of pores 19al, each of which contain oil and/or water, the oil and/or water being further comprised of a plurality of protons, each proton having a magnetic spin or magnetic moment ($u_i$) identified in FIG. 3 by the arrow A shown in FIG. 3. Since there are a plurality of protons in each of the pores 19al, there are a corresponding plurality of magnetic moments ($u_1$, $u_2$, $u_3$, ..., $u_n$) in each pore 19al, where "n" equals the number of protons in each pore.

Figure 4:
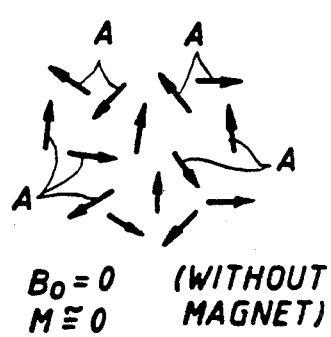

FIG. 4 illustrates a plurality of magnetic moments "$u_i$" (identified in FIG. 4 by a plurality of arrows "A") associated with a corresponding plurality of protons disposed within a particular one of the pores 19al of the volume of investigation 19 when the static magnetic field B0 is zero. Note that the magnetic moments ($u_i$) A all point in different directions. Therefore, a composite magnetic moment "M", defined to be the vector sum of all individual magnetic moments A (that is, $M = u_1 + u_2 + u_3 + ... + u_n$) is approximately zero.

Figure 5:
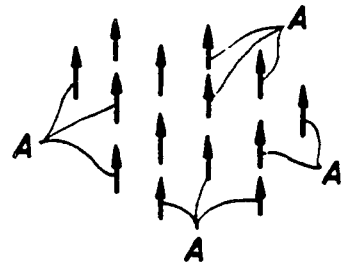

However, FIG. 5 illustrates the same plurality of magnetic moments A of FIG. 4, but now the magnetic field B0 is not equal to zero. Note that, in FIG. 5, the magnetic moments ($u_i$) A align together in the same direction when the magnetic field B0 is not equal to zero. Therefore, the composite magnetic moment "M" is not approximately equal to zero, but rather, is equal to a sum which is defined to be the sum of all individual magnetic moments A. Since each individual magnetic moment A can be quantified by the term "$u_i$", the composite magnetic moment "M" is equal to the sum of all individual magnetic moments "$u_i$", where $i = 1, 2, 3 ... , n$, associated with the "n" individual protons disposed within a pore space 19al associated with the volume of investigation 19, that is, $M = u_1 + u_2 + u_3 + ... + u_n$.

Figure 6:
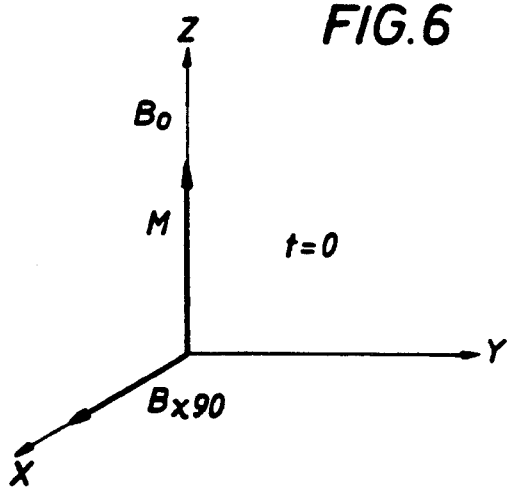
FIGS. 6–7 illustrate the effects on the proton's composite magnetic moment M of the presence of two magnetic fields: the static magnetic field B0 and a radio frequency magnetic field B$_{x90}$, the direction of which is transverse to the static magnetic field B0 and along the x-axis, the field B$_{x90}$ being applied along the x-axis for a duration "T90" which causes a 90 degree rotation of the composite magnetic moment vector M about the x-axis.

Referring to FIG. 6, assume that the composite magnetic moment "M" for the volume of investigation 19 of FIG. 3–5 is aligned along the "z" axis; assume further that the static magnetic field B0 is also aligned along the z-axis. Then, assume that an oscillating radio frequency magnetic field pulse "B1" or "$B_{x90}$" is applied along the x-axis, transverse to the z-axis.

Figure 7:
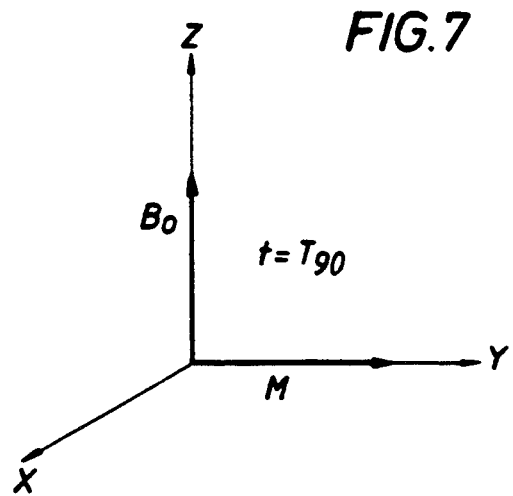

Referring to FIG. 7, recalling the assumptions mentioned above with reference to FIG. 6, since the pulse duration of the oscillating magnetic field pulse "$B_{x90}$" is 90 degrees and is applied along the x-axis in the presence of the static magnetic field B0, the composite magnetic moment "M" rotates 90 degrees from the z-axis to the y-axis, as shown in FIG. 7.

Referring to FIGS. 7a–7b, the magnetic moment vector M is initially disposed along the y-axis as shown in FIG. 7, and begins to "precess" (or rotate) clockwise within the x-y plane, as shown in FIG. 7a. However, in FIG. 7b, if an oscillating magnetic field pulse $B_{y180}$ is applied along the y-axis (for a period of time equivalent to a 180 degree pulse duration), the magnetic moment vector M rotates or flips 180 degrees from one quadrant within the x-y plane to another quadrant within the x-y plane, as illustrated by element numeral 30 in FIG. 7b. The significance of this concept will become clear with reference to FIGS. 8a–8L of the drawings.

Referring to FIG. 8a–8m, recall that the composite magnetic moment "M" is defined to be the vector sum of all the individual magnetic moments "$u_i$" (identified by the letter A) of all protons within a pore space 19al in FIG. 3, that is, $M = SUMMATION\ u_i$, where $i = 1, 2, ..., n$, or $M = u_1 + u_2 + u_3 + ... + u_n$. In FIGS. 7a–7b, it was shown that, in the presence of the static magnetic field B0, the composite magnetic moment vector M precessed in the x-y plane, then flipped to another quadrant in response to the $B_{y180}$ oscillating magnetic field pulse.

Since the composite magnetic moment vector M is the sum of all individual magnetic moment "$u_i$", in actuality, all of the individual magnetic moments "$u_i$", being disposed within the static magnetic field B0, individually precess in the x-y plane; and, then, each individual magnetic moment "$u_i$" flips to another quadrant in response to the $B_{y180}$ oscillating magnetic field pulse.

However, the static magnetic field B0 is not homogeneous, that is, some parts of the static magnetic field B0 are stronger in terms of field strength than other parts of the field B0. Therefore, if one individual magnetic moment "$u_1$" is disposed within a stronger part of the static magnetic field B0, and another individual magnetic moment "$u_2$" is disposed within a weaker part of the static magnetic field B0, the rate of precession or rotation within the x-y plane of the one magnetic moment "$u_1$" will be greater than the rate of precession or rotation within the x-y plane of the other magnetic moment "$u_2$".

FIGS. 8a–8m illustrate the effects on the precession rate of the one individual magnetic moment "$u_1$" which is located within a stronger part of the field B0 relative to another individual magnetic moment "$u_2$" which is located within a weaker part of the field B0; furthermore, FIGS. 8a–8L illustrate the effects on the one individual magnetic moment "$u_1$" and the other individual magnetic moment "$u_2$" of a further, oscillating magnetic field pulse $B_{y180}$ degrees about the y-axis thereby causing the magnetic moments "$u_1$" and "$u_2$" to refocus and to produce one of the spin-echo receiver voltage pulses of FIG. 9b.

Figure 8A:
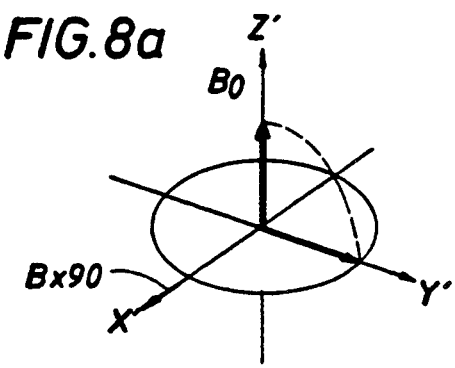
FIGS. 8a–8m illustrate the effects on the precession rate of an individual magnetic moment "A$_n$" which is located within a stronger field strength of the static magnetic field B0, relative to another individual magnetic moment "A$_f$" which is located within a weaker field strength of the static magnetic field B0, since the field B0 is non-homogeneous and the individual magnetic moments precess at different rates about the z-axis, the direction of the magnetic field B0 vector, and the effects on the magnetic moments A$_n$ and A$_f$ of a further magnetic field pulse B$_{y180}$ which "rotates" the magnetic moments A$_n$ and A$_f$ 180 degrees about the y-axis thereby causing the magnetic moments A$_n$ and A$_f$ to refocus and to produce the spin-echo receiver voltage pulses of FIG. 9b.

In FIG. 8a, the plurality of individual magnetic moments "$u_i$" A (and thus, the composite magnetic moment M) rotate 90 degrees in the z-y plane, as shown in FIGS. 6–7 of the drawings, in response to the static, radio frequency magnetic field pulse "$B_{x90}$" which is applied along the x-axis for a time equivalent to a 90 degree pulse duration.

Figure 8B:
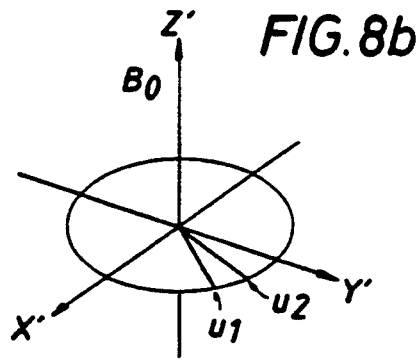

In FIG. 8b, the one individual magnetic moment "$u_1$", the magnetic moment associated within one particular proton which is disposed within a stronger part of the magnetic field B0, precesses or rotates, in a clockwise direction, at a faster rate than does the other individual magnetic moment "$u_2$", the other individual magnetic moment associated with another proton that is located within a weaker part of the magnetic field B0.

Figure 8C:
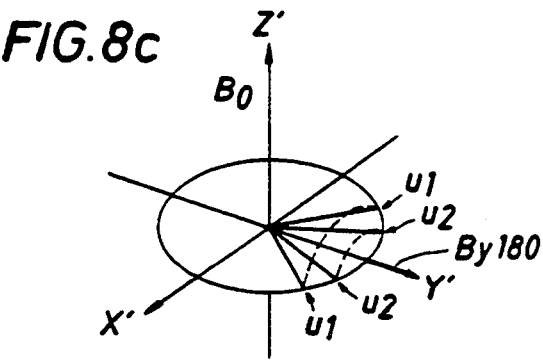
Figure 8D:
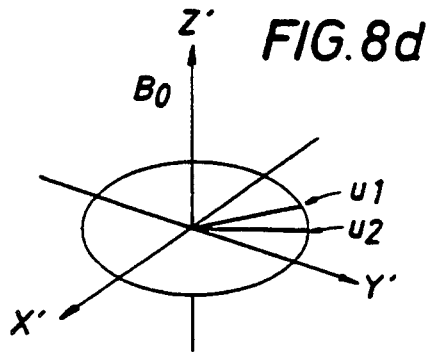
Figure 8E:
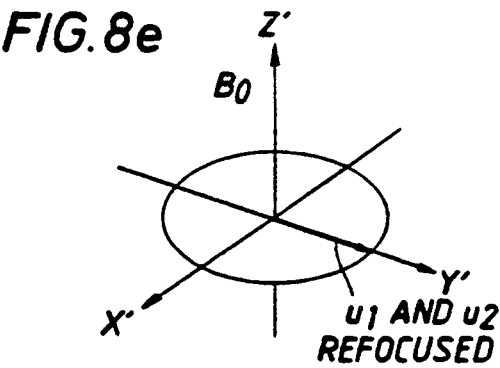
Figure 8F:
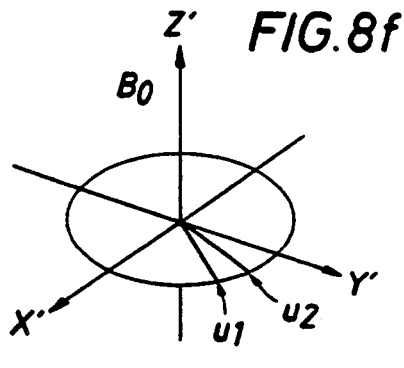
Figure 8G:
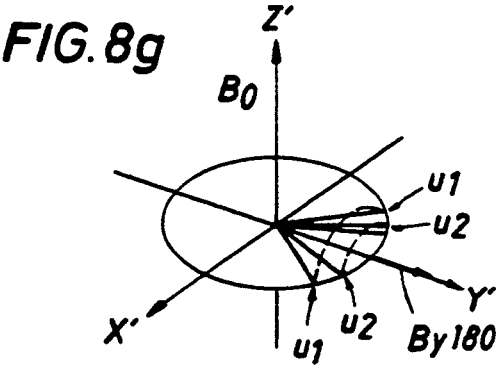
Figure 8H:
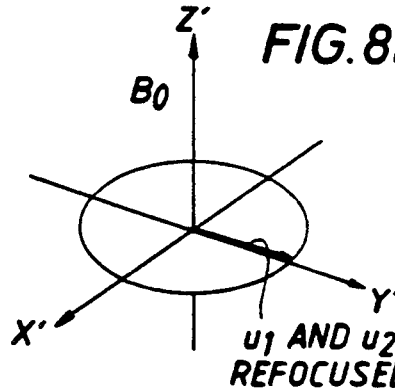
Figure 8I:
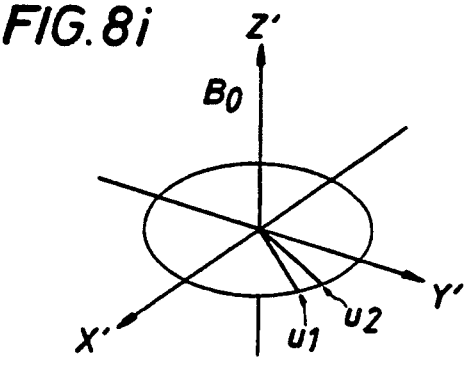
Figure 8J:
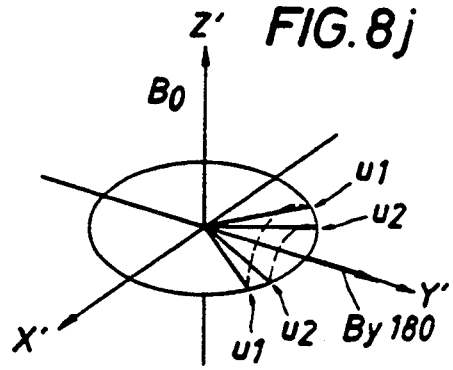
Figure 8K:
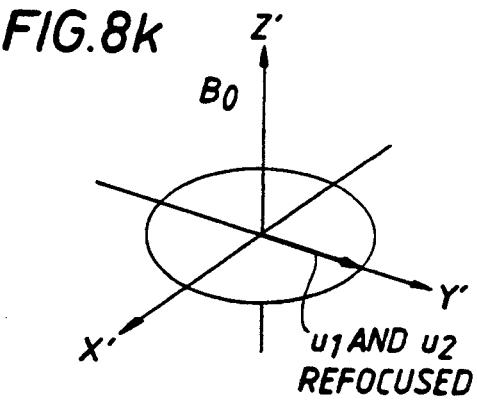
Figure 8L:
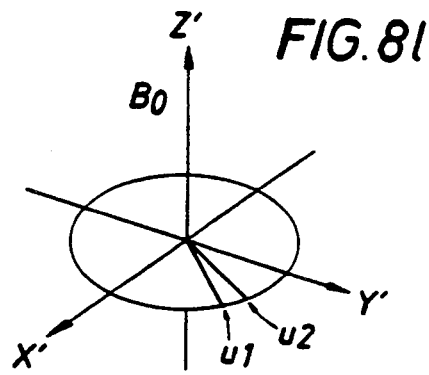
Figure 8M:
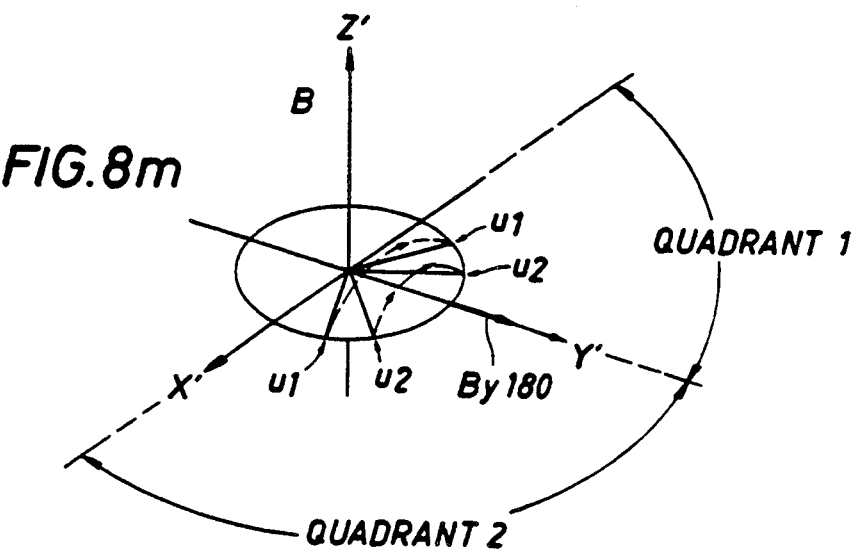

In FIGS. 8c and 8m, a further, oscillating magnetic field pulse $B_{y180}$ is applied at a time $t_{cp}$ after application of the magnetic field pulse $B_{x90}$ (which is assumed to be applied at a time t=O) along the y-axis for a period of time equivalent to a pulse duration of 180 degrees; in response to the further magnetic field pulse $B_{y180}$, the individual magnetic moments "$u_1$" and "$u_2$" rotate or flip about the y-axis by an amount equal to 180 degrees thereby removing the two individual magnetic moments "$u_1$" and "$u_2$" from quadrant number 2 and locating the two individual magnetic moments "$u_1$" and "$u_2$" in quadrant number 1 of the x-y plane, as shown in FIG. 8c.

In FIG. 8d, both of the individual magnetic moments "$u_1$" and "$u_2$" continue to rotate in the clockwise direction but the one magnetic moment "$u_1$" continues to rotate or precess at a faster rate than does the other magnetic moment "$u_2$".

In FIG. 8e, since, as shown in FIG. 8c, the two individual magnetic moments "$u_1$" and "$u_2$" flipped from quadrant 2 to quadrant 1 of the x-y plane in response to the oscillating magnetic field $B_{y180}$, the two individual magnetic moments "$u_1$" and "$u_2$" refocus (align together as one magnetic moment vector) thereby producing a first spin-echo signal (echo 1) at a time $2t_{cp}$, which spin-echo signal is picked up by the antennas 18 or 21 of the NMR tool 13 of FIG. 1 and is transmitted uphole to the processing system 7a. The first spin-echo signal (echo 1) is shown in FIG. 9b of the drawings.

In FIG. 8f, the one magnetic moment "$u_1$" proceeds to precess ahead or in front of the other magnetic moment "$u_2$" since the rate of precession of the one magnetic moment "$u_1$" is still greater than the rate of precession of the other individual magnetic moment "$u_2$".

In FIGS. 8g and 8m, a further oscillating magnetic field pulse $B_{y180}$ is applied at a time $3t_{cp}$ along the y-axis for a period of time equivalent to a pulse duration of 180 degrees; in response to the further magnetic field pulse $B_{y180}$, the two individual magnetic magnetic moments "$u_1$" and "$u_2$" rotate or flip about the y-axis by an amount equal to 180 degrees (similar to the action depicted in FIG. 8c) thereby removing the two magnetic moments "$u_1$" and "$u_2$" from quadrant number 2 and locating the two magnetic moments "$u_1$" and "$u_2$" into quadrant number 1 of the x-y plane, as shown in FIG. 8g.

In FIG. 8h, the two individual magnetic moments "$u_1$" and "$u_2$" refocus again, similar to the action depicted in FIG. 8e, thereby producing a second spin-echo signal (echo 2) at a time $4t_{cp}$, which second spin-echo signal is picked up by antennas 18 and 21 of the NMR tool 13 of FIG. 1 and transmitted uphole to the processing system 7a. FIG. 9b illustrates the echo 2, second spin-echo signal.

In FIG. 8i, the one individual magnetic moment "$u_1$" proceeds ahead of the other individual magnetic moment "$u_2$" since the rate of precession of the one magnetic moment "$u_1$" is greater than the rate of precession of the other magnetic moment "$u_2$".

In FIGS. 8j and 8m, the two individual magnetic moments "$u_1$" and "$u_2$" flip or rotate 180 degrees about the y-axis from quadrant 2 to quadrant 1 of the x-y plane in response to application of the oscillating magnetic field pulse $B_{y180}$, applied along the y-axis at a time $5t_{cp}$.

In FIG. 8k, the two individual magnetic moments "$u_1$" and "$u_2$" refocus again thereby producing a third spin-echo signal (echo 3) at a time $6t_{cp}$, which third spin-echo signal (echo 3) is picked up by antennas 18 and 21 of NMR tool 13 and transmitted uphole to processing system 7a. The echo 3, third spin-echo signal is illustrated in FIG. 9b.

In FIG. 8L, the one individual magnetic moment "$u_1$" proceeds ahead of the other individual magnetic moment "$u_2$" since the rate of precession of the one magnetic moment "$u_1$" is greater than the rate of precession of the other magnetic moment "$u_2$".

Therefore, three spin-echo signals have been produced, the first spin-echo signal (echo 1) being produced in connection with FIG. 8e, the second spin-echo signal (echo 2) being produced in connection with FIG. 8h, and the third spin-echo signal (echo 3) being produced in connection with FIG. 8k.

Referring to FIGS. 9a–9b, the aforementioned first and second spin-echo signals, echo 1 and echo 2, are illustrated in time relation to the oscillating magnetic field pulse $B_{x90}$ (90 pulse) which is directed along the x-axis of FIG. 6 and has a pulse duration of 90 degrees, and to the further oscillating magnetic field pulse $B_{y180}$ (180 pulse) directed along the y-axis and having a pulse duration of 180 degrees. FIG. 9b illustrates a plurality of spin-echo signals associated with either the ($R_j$) inphase channel or the ($X_j$) quadrature channel. When FIGS. 9a–9b are examined jointly with FIGS. 8a–8m, it is evident that the nth spin-echo signal is produced at a time $2(n)t_{cp}$ following application of the magnetic field pulses $B_{y180}$ at $(2n-1)t_{cp}$, where $n=1, 2, 3, \ldots, J$. The first spin-echo signal (echo 1) is generated after a time $t_{cp}$ elapses following application of the first magnetic field pulse $B_{y180}$ and the second spin-echo signal (echo 2) is generated after a time $t_{cp}$ elapses following application of the second magnetic field pulse $B_{y180}$.

Referring to FIG. 10, a nuclear magnetic resonance (NMR) logging system is illustrated, the logging system including a NMR logging tool 13 disposed in a wellbore and surface equipment 7 in the form of a well logging truck 7 situated on the surface of the wellbore, the well logging truck 7 including a processing system 7a in the form of a computer 7a situated within the well logging truck 7.

In FIG. 10, the NMR logging tool 13 includes antennas 18 and 21 and an electronics cartridge 24 responsive to signals received by the antennas 18 and 21 for processing the signals before transmission of the signals uphole to the computer 7a in the well logging truck. The electronics cartridge 24 of the logging tool 13 stores a first part of the signal processing (software) method and apparatus in accordance with one aspect of the present invention, and the computer 7a stores a second part of the signal processing (software) method and apparatus in accordance with another aspect of the present invention.

Figure 16:
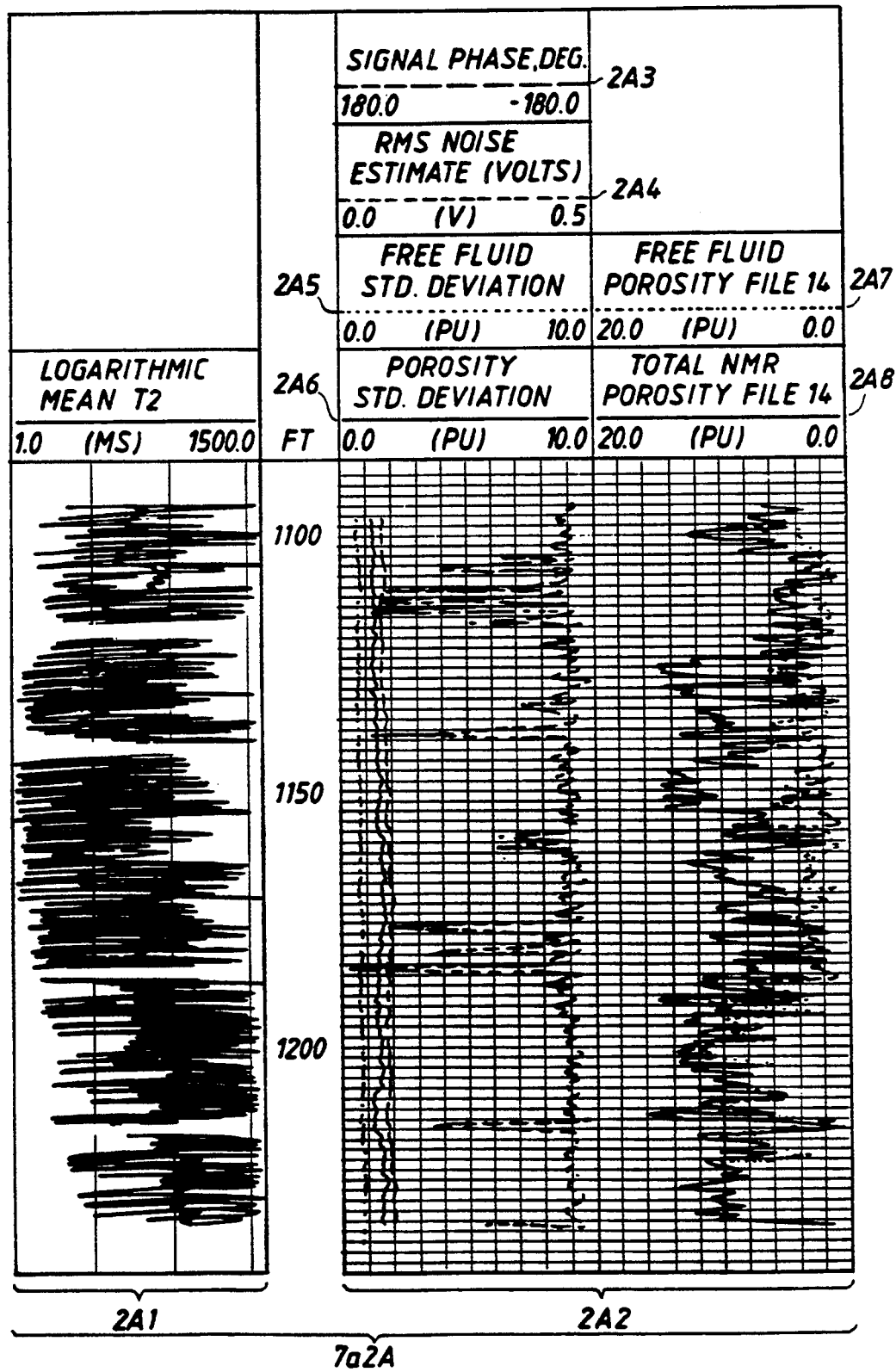
FIG. 16 illustrates a new output record medium, comprising a plurality of new logs, generated by the processing system disposed at the wellbore surface in accordance with another aspect of the present invention.

In FIG. 11, the computer 7a includes a system bus 7a1, a processor 7a3 connected to the system bus 7a1 for generating new output data in accordance with one aspect of the present invention, a memory 7a4 connected to the system bus 7a1 for storing the second part of the signal processing (software) method and apparatus of the present invention, and a recorder 7a2 connected to the system bus for receiving the new output data from the processor and generating a new output record medium 7a2A, to be discussed with reference to FIG. 16 of the drawings, in accordance with another aspect of the present invention. The computer 7a may include or consist of any one of the following computer systems manufactured by Digital Equipment Corporation (DEC), Maynard, Mass.: (1) DEC VAX 6430, (2) DEC PDP-11, or (3) DEC Vaxstation 3100, or it may include any other suitable computer system.

Referring to FIGS. 12a, 12b1, and 12b2, a contruction of the electronics cartridge 24 of FIG. 10 is illustrated. A more detailed construction of the hardware associated with the NMR logging system of FIGS. 1, 12a, 12b1, and 12b2, and in particular, of the construction of the electronics cartridge 24, is set forth in a prior pending application entitled "Borehole Measurement of NMR Characteristics of Earth Formations", corresponding to attorney docket number 20.2610, filed Nov. 2, 1992, the disclosure of which is incorporated by reference into this specification.

In FIG. 12a, the surface computer 7a is electrically connected via logging cable to the electronics cartridge 24 of FIG. 10. The electronics cartridge 24 includes a downhole computer 46. The downhole computer 46 is ultimately electrically connected to the antennas 18 and 21.

In FIGS. 12b1, the downhole computer 46 of electronics cartridge 24 includes a system bus 46b to which a processor 46c is electrically connected and a memory 46a is electrically connected.

In FIG. 12b2, the memory 46a stores the first part of the signal processing method and apparatus of the present invention.

Figure 13:
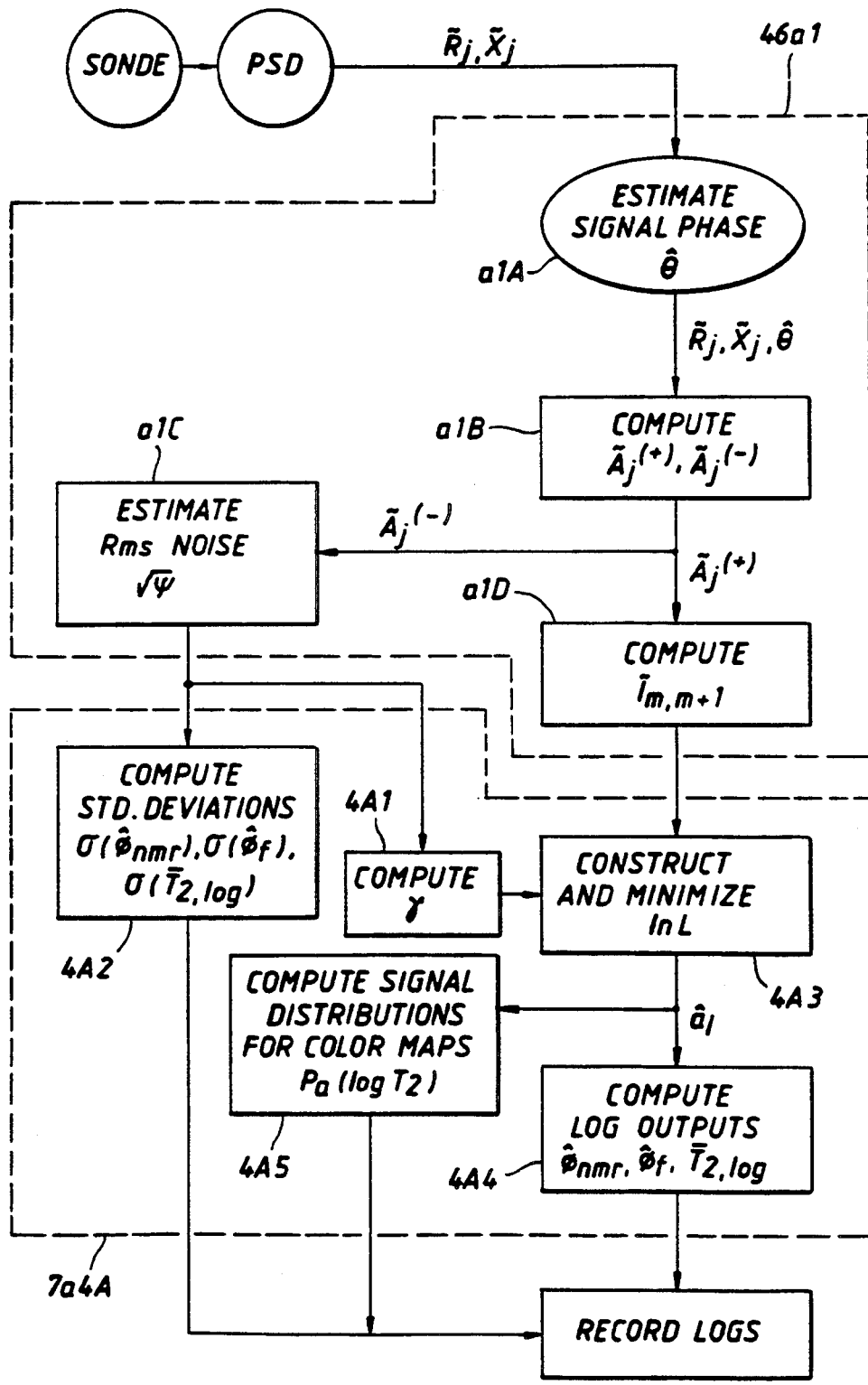
FIG. 13 illustrates a block diagram or flow chart of the first part of the signal processing method and apparatus of the present invention stored in the electronics cartridge of the NMR tool and the second part of the signal processing method and apparatus of the present invention stored in the surface oriented processing system of FIG. 10, which first part and second part of the signal processing method and apparatus is embodied in the form of software stored in a memory of the electronics cartridge and the surface oriented processing system, respectively.

Referring to FIG. 13, a flow chart of the first part and the second part of the signal processing (software) method and apparatus of the present is illustrated.

This specification is divided into a Description of the Preferred Embodiment, and a Detailed Description of the Preferred Embodiment. The flow chart of FIG. 13 and the following discussion is part of the Description of the Preferred Embodiment and provides a general discussion of the signal processing method and apparatus of the present invention. The Detailed Description of the Preferred Embodiment set forth below provides a more detailed discussion of the aforementioned signal processing method and apparatus of the present invention. In the following general discussion, occasional reference to equations and other specific description set forth in the Detailed Description of the Preferred Embodiment will be required.

The signal processing method and apparatus of the present invention, embodied in the form of a software package, includes two parts: a first part 46a1 stored in the memory 46a of the downhole computer 46 of electronics cartridge 24 of FIGS. 12a–12b2 and a second part 7a4A stored in the memory 7a4 of the well logging truck computer 7a of FIG. 10 situated at the surface of the wellbore.

In FIG. 1, the receiving antennas 18 and 21 of logging tool 13 measure the magnetic moments of individual protons in the volumes 19 and 22 of the formation traversed by the borehole 10 and generate a plurality of spin-echo receiver voltage pulses (FIG. 9b) representative of the magnetic moments. The electronics cartridge 24 begins processing the two-channel receiver voltage pulses by integrating each of the spin-echo receiver voltage pulses over a time interval, there being a total of J time intervals, each time interval being centered about a time $t_j = j$ delta, where $j = 1, 2, \ldots, J$. The integrated signals are recorded as spin-echo inphase ($R_j$) and quadrature ($X_j$) amplitudes, time series channels or waveforms.

Referring to FIG. 13, the first part 46a1 of the signal processing method and apparatus of the present invention is illustrated.

In FIG. 13, the first part 46a1 of the signal processing method and apparatus of the present invention receives the aforementioned inphase ($R_j$) and quadrature ($X_j$) amplitudes, and a signal phase (theta) is estimated associated with these amplitudes, block a1A. Equation 9 of the Detailed Description set forth below provides the equation of the signal phase (theta) as a function of the inphase ($R_j$) and quadrature ($X_j$) amplitudes, as follows:

$$\theta = \arctan\left[\frac{\sum_{j=1}^{J} X_j}{\sum_{j=1}^{J} R_j}\right], \quad (9)$$

Since the inphase ($R_j$) amplitude, the quadrature ($X_j$) amplitude, and the signal phase (theta) is known for each spin-echo receiver voltage pulse, the signal plus noise amplitude $A_j(+)$ and the amplitude $A_j(-)$, for each spin-echo receiver voltage pulse, may now be determined, block a1B, by utilizing equations 22 and 23 of the Detailed Description, as follows:

$$A_j^{(+)} = R_j \cos\theta + X_j \sin\theta, \quad (22)$$

$$A_j^{(-)} = R_j \sin\theta - X_j \cos\theta. \quad (23)$$

The RMS noise, the square root of psi or "SQRT psi", can be estimated from the signal plus noise amplitude $A_j^{(-)}$, block a1C, by utilizing a practical implementation of equation 31 of the Detailed Description, as follows:

1/J SUMMATION (j=1 . . . J) $(A_j^{(-)})^2$ approximately=psi, where equation (31) is set forth as follows:

$$\{(A_j^{(-)})^2\} \approx \psi, \quad (31)$$

The window sum $I_{m,m+1}$ can be computed from the signal plus noise amplitude $A_j^{(+)}$, block a1D, by utilizing equations 22 and 35 of the Detailed Description, as follows:

$$I_{m,m+1} = \sum_{j=N_m+\rho_m}^{N_{m+1}} A_j^{(+)}, \quad (35)$$

As a result, when the downhole computer 46 of FIG. 12 executes the first part 46a1 of the signal processing software of FIG. 13, two outputs are generated: the window sum $I_{m,m+1}$ which is determined from equation 35 and the RMS noise (SQRT psi) which is determined from equation 31.

The following paragraphs present a more detailed explanation of the window sum $I_{m,m+1}$ determined from equation 35.

Figure 14:
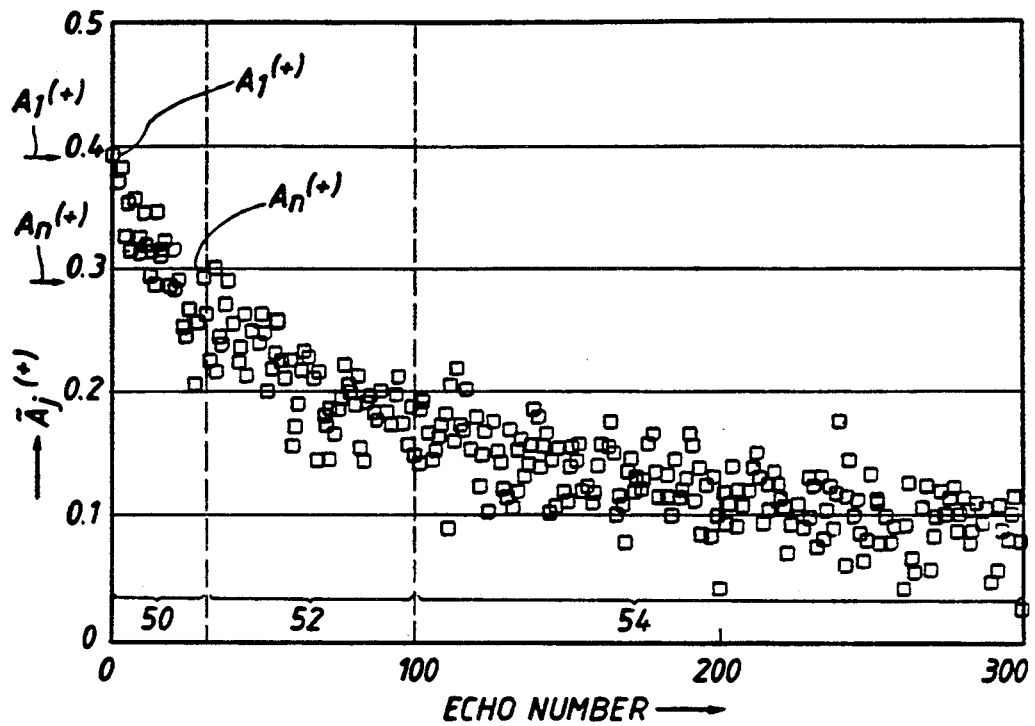
FIG. 14 illustrates a plurality of the spin-echo signal plus noise amplitudes $A_j^{(+)}$ corresponding, respectively, to the plurality of spin-echo signals of FIG. 9b, each spin-echo signal plus noise amplitude $A_j^{(+)}$ being identified by an echo number, the echo numbers being divided into a plurality of time windows.

Referring to FIG. 14, an example of signal plus noise amplitudes $A_j^{(+)}$ that have been determined from spin-echo signals (echo 1, echo 2, . . . ) like those shown schematically as either R or X channel spin-echo pulses in FIG. 9b is illustrated in FIG. 14. The spin-echo signal plus noise amplitudes $A_j^{(+)}$ are separated in time by "$2t_{cp}$" from each other.

Figure 15:
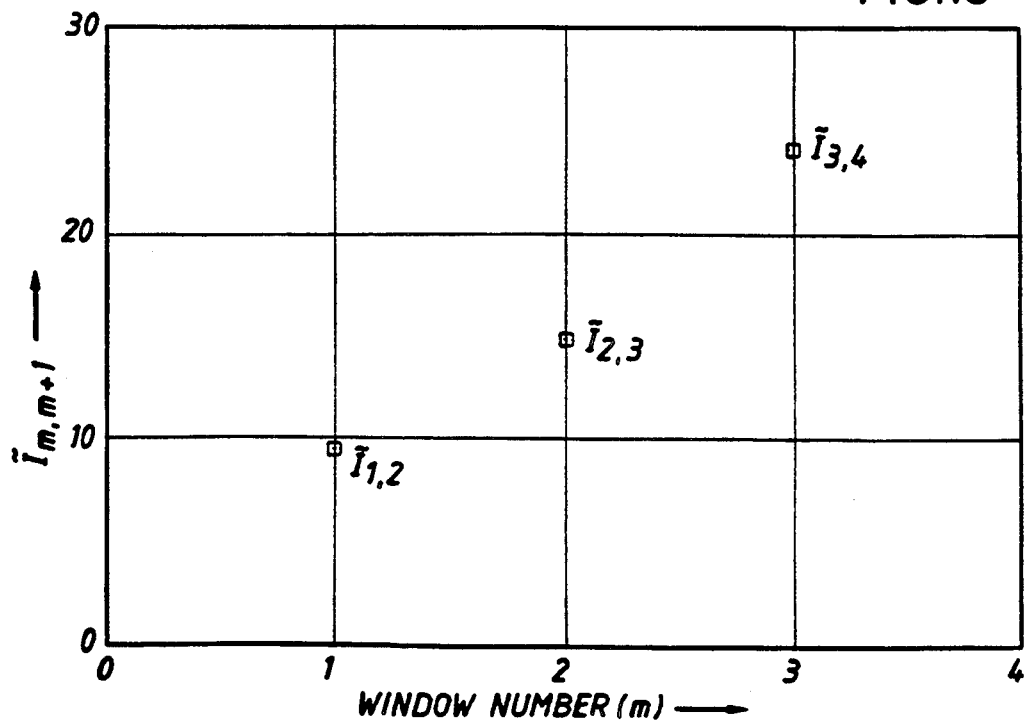
FIG. 15 illustrates a plurality of window sums $I_{m,m+1}$ corresponding, respectively, to the plurality of time windows of FIG. 14.

Referring to FIGS. 14 and 15, the technique for determining a particular window sum ($I_{m,m+1}$) from a plurality of signal plus noise amplitudes ($A_1^{(+)}$, $A_2^{(+)}$, $A_3^{(+)}$, $A_4^{(+)}$, . . . , $A_n^{(+)}$) is illustrated.

Recalling that a window sum $I_{m,m+1}$ is determined from the equation "$I_{m,m+1}$=SUMMATION $A_j^{(+)}$", as set forth in equation 35 of the Detailed Description of the Preferred Embodiment set forth below, referring to FIG. 14 and 15, a first window sum "$I_{1,2}$", where m=1, may be determined by summing a plurality of individual signal plus noise amplitudes $A_1^{(+)}$, $A_2^{(+)}$, $A_3^{(+)}$, $A_4^{(+)}$, . . . , $A_n^{(+)}$ which are disposed within a first time window 50 shown in FIG. 14. A second window sum $I_{2,3}$ is determined in association with a second time window 52 and a third window sum $I_{3,4}$ is determined in association with a third time window 54 in the same manner as indicated above by summing the associated signal plus noise amplitudes $A_j^{(+)}$ which are disposed within the second and third time windows, respectively.

The window sums are transmitted uphole from the NMR tool 13 of FIGS. 1 and 10 to the processing system or well logging truck computer 7a disposed on the wellbore surface as shown in FIG. 10. There are $N_w$ window sums, where $N_w$ is typically three to five in number. Therefore, since only $N_w$ window sums are being transmitted uphole instead of 2J amplitudes (there being $R_j$ amplitudes and $X_j$ amplitudes, where j=1, 2, 3, . . . ,J), the telemetry requirements needed to transmit the $N_w$ window sums uphole to the truck computer 7a, relative to the telemetry requirements needed to transmit the 2J amplitudes uphole, is significantly reduced.

Referring again to FIG. 13, the second part 7a4A of the signal processing method and apparatus of the present invention is illustrated.

In FIG. 13, recall that the RMS noise (SQRT psi) is output from the first part 46a1 of the signal processing method and apparatus of the present invention. The RMS noise is used for two purposes:

1. to compute "gamma", block 4A1—the computation of "gamma" is discussed in connection with equation (42) of the Detailed Description and is set forth in Appendix A of the Detailed Description of the Preferred Embodiment, entitled "An Algorithm for Optimal Selection of gamma"; in Appendix A, note that the best value of "gamma" can be found by finding the roots of equation (A.26) or of similarly derived equations; and
2. to compute standard deviations "sigma($phi_{nmr}$)", "sigma($phi_f$)", and "sigma($T_{2,log}$)", block 4A2—the standard deviation "sigma($phi_{nmr}$)" may be determined from equation (58) of the Detailed Description of the preferred embodiment set forth below; the standard deviation "sigma($phi_f$)" may be determined from equation (61) of the Detailed Description; and the standard deviation "sigma($T_{2,log}$)" may be determined from equation (65) of the Detailed Description set forth below.

The parameter "gamma", computed in block 4A1, is used to construct and minimize the likelihood function ($-\ln L$), block 4A3. The likelihood function ($-\ln L$) is represented by the following equation, which is equation (42) of the Detailed Description set forth below:

$$-\ln L = \sum_{m=1}^{N_\omega} \frac{(I_{m,m+1} - I_{m,m+1}\{a_l\})^2}{2\psi[N_{m+1} - N_m + \delta_{m,1}]} + \frac{\gamma}{2\psi} \sum_{l=1}^{N_c} a_l^2, \quad (42)$$

The spectral amplitudes $\{a_l\}$ are determined by minimization of equation (42) subject to a positivity constraint, as indicated in the Detailed Description set forth below in connection with equation 42.

The spectral amplitudes $\{a_l\}$ are used for two purposes: to compute log outputs "$phi_{nmr}$", "$phi_f$", and $T_{2,log}$; and to compute signal distributions $P_a(\log T_2)$ represented by color maps 2A1 of FIG. 16, to be discussed below.

To compute log outputs "$phi_{nmr}$", "$phi_f$", and $T_{2,log}$, block 4A4, the log output "$phi_{nmr}$" is determined from equation (43), as follows:

$$\phi_{nmr} = K_{tool} \int_{T_{min}}^{T_{max}} dT_2 P(T_2) = K_{tool} \sum_{l=1}^{N_c} a_l, \quad (43)$$

The log output "$phi_f$" is determined from equation (44), as follows:

$$\phi_f = K_{tool} \sum_{l=N_c}^{N_c} a_l + \Delta\phi, \quad (44)$$

The log output $T_{2,log}$ is determined from equations (54) and (55), as follows:

$$m = \frac{\sum_{l=1}^{N_c} \delta P_a(\log T_{2,l}) \log T_{2,l}}{\sum_{l=1}^{N_c} \delta P_a(\log T_{2,l})} = \frac{\sum_{l=1}^{N_c} a_l \log T_{2,l}}{\sum_{l=1}^{N_c} a_l} \quad (54)$$

$$T_{2,log} = 10^{r^2}. \quad (55)$$

To compute signal distributions $P_a(\log T_2)$ which represent color maps 2A1 of FIG. 16, block 4A5, the computation of the signal distributions $P_a(\log T_2)$ is performed using equation (50) as follows:

$$P_a(\log T_{2,l}) = \frac{2a_l r}{c(r^2 - 1)}. \quad (50)$$

Referring to FIG. 16, a new output record medium 7a2A is illustrated. This new output record medium, a new log adapted to be given to a client for evaluation of the formation traversed by the wellbore, is generated in response to the receipt of the following information:

1. the log outputs "phi$_{nmr}$", "phi$_f$", and T$_{2,log}$ of block 4A4;
2. the signal distributions for color maps $P_a(\log T_2)$ of block 4A5; and
3. the standard deviations "sigma(phi$_{nmr}$)", "sigma(phi$_f$)", and "sigma(T$_{2,log}$)" of block 4A2.

The new output record medium 7a2A of FIG. 16 records the following new data or information presented in the form of logs as a function of depth in the wellbore (see element 2A2 in FIG. 16) and in the form of a color map (see element 2A1 of FIG. 16):

1. signal phase 2A3 from block a1A;
2. RMS noise estimate 2A4 from block a1C;
3. free fluid standard deviation 2A5 from block 4A2;
4. porosity standard deviation 2A6 from block 4A2;
5. free fluid porosity 2A7 from block 4A4;
6. total NMR porosity 2A8 from block 4A4; and
7. color Map 2A1.

The new output record medium 7a2A is given to a customer or client for the purpose of determining the presence or absence of underground deposits of hydrocarbons and the reservoir quality of the formation traversed by the wellbore 10 of FIG. 1.

A functional description of the operation of the signal processing method and apparatus in accordance with the present invention is set forth in the following paragraphs with reference to FIG. 16a and FIG. 13 of the drawings.

In FIGS. 16a and 13, the RF antennas 18 and/or 21 measure the precession of the protons in the pores 19a1 of the volume of investigation 19 of FIG. 3 and generate spin-echo receiver voltage pulses similar to the spin-echo receiver voltage pulses "echo 1", "echo 2", and "echo 3" illustrated in FIG. 9b of the drawings. Phase sensitive detection (PSD) circuits disposed within the electronics cartridge 24 integrate each of the spin echo receiver voltage pulses over a time interval, and the integrated signals are recorded as spin-echo inphase (R$_j$) and quadrature (X$_j$) amplitudes. The processor 46c of the downhole computer 46 in the electronics cartridge 24 disposed within the NMR tool 13 in the wellbore begins executing the first part 46a1 of the signal processing (software) method and apparatus of FIG. 13 stored within the memory 46a of the downhole computer 46. When the processor 46c completes the execution of the first part of the signal processing software 46a1 stored in memory 46a, the following data and information is determined:

1. the signal phase (theta) is estimated from the 2J inphase (R$_j$) and quadrature (X$_j$) amplitudes corresponding to J spin-echo receiver voltage pulses in the R and X channels using equation 9 as a function of the inphase and quadrature amplitudes set forth in the detailed description, block a1A of FIG. 13;
2. a spin-echo signal plus noise amplitude A$_j^{(+)}$ is determined for each inphase (R$_j$) amplitude, quadrature (X$_j$) amplitude, and signal phase (theta) using equation 22 in the Detailed Description; and the amplitude A$_j^{(-)}$ is also determined from inphase (R$_j$) amplitude, quadrature (X$_j$) amplitude, and signal phase (theta) using equation 23 in the Detailed Description, block a1B of FIG. 13; furthermore, there are J inphase amplitudes (R$_j$) and J quadrature amplitudes (X$_j$); and, as a result, there are J spin-echo signal plus noise amplitudes A$_j^{(+)}$ and there are J amplitudes A$_j^{(-)}$;
3. the N$_w$ window sums I$_{m,m+1}$ are determined from the A$_j^{(+)}$ signal plus noise amplitudes using equation 35, where N$_w$ is typically three to five in number, thereby reducing telemetry requirements for transmission of window sums uphole to the surface computer 7a, block a1D of FIG. 13; and
4. the RMS noise SQRT PSI is determined from the J amplitudes A$_j^{(-)}$ using the practical implementation of equation 31 or equation per se, block a1C of FIG. 13.

Two sets of data are transmitted uphole from the NMR tool 13 to the surface computer 7a: the N$_w$ window sums I$_{m,m+1}$ and the RMS noise SQRT PSI.

The processor 7a3 of the surface computer 7a receives the N$_w$ window sums I$_{m,m+1}$ and the RMS noise SQRT PSI from the downhole computer 46 of the NMR tool 13 disposed downhole; in response, the processor 7a3 begins to execute the second part of the signal processing software 7a4A of FIG. 13 stored in memory 7a4 of the surface computer 7a. When the processor 7a3 completes execution of the second part of the signal processing software 7a4A, the following additional data and information is determined:

1. the standard deviations "sigma(phi$_{nmr}$)", "sigma(phi$_f$)", and "sigma(T$_{2,log}$)" are determined, block 4A2 of FIG. 13, the standard deviation "sigma(phi$_{nmr}$)" being determined from equation (58) of the Detailed Description, the standard deviation "sigma(phi$_f$)" being determined from equation (61) of the Detailed Description, and the standard deviation "sigma(T$_{2,log}$)" being determined from equation (65) of the Detailed Description of the Preferred Embodiment set forth below.
2. the parameter "gamma" is determined from the RMS noise SQRT PSI, block 4A1 of FIG. 13, in the manner described in Appendix A of the Detailed Description and in connection with equation 42 in the Detailed Description;
3. once the parameter "gamma" is determined, a likelihood function (−ln L) is constructed and minimized, the likelihood function being represented by equation 42 of the Detailed Description, which equation is a function of the parameter "gamma", block 4A3 of FIG. 13;
4. the spectral amplitudes {a$_1$} are determined by minimization of the likelihood function (−ln L) of equation 42, and the spectral amplitudes {a$_1$} are used for two purposes: to compute log outputs "phi$_{nmr}$", "phi$_f$", and T$_{2,log}$, block 4A4 of FIG. 13, and to compute the signal distributions P$_a$(log T$_2$), which signal distributions are illustrated in the form of the color maps 2A1 of FIG. 16, block 4A5 of FIG. 13;

The processor 7a3 of FIG. 16a instructs the recorder 7a2 to generate the new output record medium 7a2A of FIG. 16 using the aforementioned recently determined standard deviations "sigma(phi$_{nmr}$)", "sigma(phi$_f$)", and "sigma(T$_{2,log}$)"; the signal distributions P$_a$(log T$_2$); and the log outputs "phi$_{nmr}$", "phi$_f$", and T$_{2,log}$, the new output record medium 7a2A of FIG. 16 displaying the following new information:

1. signal phase 2A3 from block a1A;
2. RMS noise estimate 2A4 from block a1C;
3. free fluid standard deviation 2A5 from block 4A2;
4. porosity standard deviation 2A6 from block 4A2;
5. free fluid porosity 2A7 from block 4A4;
6. total NMR porosity 2A8 from block 4A4; and
7. color map 2A1.

DETAILED DESCRIPTION OF THE PREFERRED EMBODIMENT

Introduction

The development of Pulsed Nuclear Magnetic Resonance logging tools to acquire downhole spin-echo measurements in earth formations penetrated by boreholes is a new technology. The measurement principles and pulse sequences have been recently published.[1,2] This new logging technology provides detailed formation evaluation information previously obtainable only from costly laboratory analysis of conventional core data. This information presently includes but is not limited to: (1) total NMR porosity ($\phi_{nmr}$), (2) free-fluid porosity ($\phi_f$) (i.e., part of total porosity which is movable), (3) bound fluid porosity ($\phi_b$), (4) spin-spin (T$_2$) relaxation time distributions which are related to pore size distributions in sandstones, and (5) continuous permeability logs in sandstones. To extract this information from the measured spin-echoes requires a signal processing algorithm which is capable of providing an accurate and repeatable spectral decomposition of the measured data. The algorithm must be efficient and robust for real time processing of data as it is continuously acquired by a moving logging tool. This report describes a new algorithm which statisfies these conditions and provides PNMT logs which agree well with conventional core and other log data. Other approaches to spectral decomposition of NMR data have been reported[3-6]. Kenyon, et al.[5] used the algorithm reported by Gallegos and Smith[3] to compute T$_1$ distributions in rocks from laboratory NMR inversion recovery data. Latour, et al.[6] used a computationally expensive singular value decomposition algorithm to compute relaxation time distributions in rocks from laboratory NMR data.

It is well-known that sedimentary rocks have a distribution of pore sizes. This results in NMR signals in rocks which decay with a distribution of relaxation times. Mathematically, the signal processing problem is to determine the distribution functions from the measured data (i.e., solve an inverse problem). The aforementioned formation evaluation parameters are computed from the distribution functions. Generally, there exists a joint distribution function, i.e., a function of both the longitudinal (T$_1$) and transverse (T$_2$) spin relaxation times, however, laboratory measurements have shown that these distributions in sedimentary rocks are correlated.[6] The correlation is valid at NMR frequencies in the range of 2 MHz and is applicable to the borehole measurements described in this report.

Pulse Sequence And Parameters

It suffices to describe the pulse sequence and typical measurement parameters used in practice. The spin-echo measurement employed is the well-known Carr-Purcell-Meiboom-Gill (CPMG) sequence. This sequence measures the decay of the amplitude of the transverse magnetization following a 90° (+x) r.f. pulse which rotates the magnetization into a plane transverse to an applied static magnetic field (H$_0$z). The frequency of the r.f. pulses is equal to the median Larmor proton precession frequency. The nuclear spins contributing to the transverse magnetization precess at different Larmor frequencies in the inhomogeneous d.c. magnetic field. The free-induction decay (FID) signal which is generated by the 90° (+x) pulse decays to zero within microseconds because of spin dephasing produced by the spread in Larmor frequencies. The FID signal occurs too soon following the 90° (+x) to be measured by the PNMT electronics. At times $t_j=(2j-1)t_{cp}$ following the 90° (+x) pulse, a set of 180° (y) r.f. pulses are applied which cause the transverse magnetization to refocus at times $t_j=2jt_{cp}$ for j=1, 2, . . . , J producing J spin-echo signals. Note that the r.f. magnetic field of the 180° pulses is transverse to both H$_0$ and the r.f. magnetic field of the 90° pulses. The spin-echoes are equally spaced in time with spacing $\Delta=2t_{cp}$. The train of spin-echoes represents a signal whose decay contains contributions from all components of the intrinsic T$_2$-distribution. Here intrinsic refers to a distribution that includes effects of microscopic spin-spin interactions as observed in bulk liquids as well as surface relaxation from the confining pores. It is the latter effects that frequently dominate in reservoir rocks and provide the link between T$_2$-distributions and pore size distributions. The effects, on the spin-echo decay, of molecular diffusion in the static field gradient can be made negligble for the PNMT by making the Carr-Purcell time $t_{cp}$ sufficiently short. The CPMG sequence described above can be improved by using phase alternated pairs (PAPS) of CPMGs to eliminate baseline shifts. Phase alternated pairs of CPMGs differ by shifting the phase of the 90° pulses by 180 degrees. The PNMT PAPS pulse sequences can therefore be written succinctly in an obvious notation, $$CPMG^{(\pm)}\cdot W - 90°(\pm x) - (t_{cp} - 180°(y) - t_{cp} - (echo))_{j=1,2,\ldots,J} \quad (1)$$

where W is a wait time that must precede each CPMG so that the longitudinal magnetization can recover prior to the initial 90° pulse. The PAPS pairs are combined by taking one-half their difference. This eliminates baseline offsets. Note each PAPS is constructed by signal averaging two CPMG sequences which reduces the rms noise by a factor $\sqrt{2}$.

Typical values of the pulse parameters are $t_{cp}=100-500$ μs, W=0.5-1.5 s, and J=100-1000 echoes.

Statement of The Signal Processing Problem

The spin-echo amplitudes are obtained by hardware integration of the receiver voltages over J time windows each centered about $t_j=j\Delta$ for j=1, 2, . . . , J. The PNMT tool uses phase sensitive detection to measure the in-phase ($\bar{R}_j$) and quadrature ($\bar{X}_j$) components of the signal-plus-noise amplitudes. As shown in the next section, the signal phase $\theta$ is estimated from the $\bar{R}_j$ and $\bar{X}_j$ amplitudes which are then combined to provide the signal-plus-noise amplitudes $\bar{A}_j(\pm)$. A phenomenological model for the signal-plus-noise amplitude of the j-th echo can be written in the form:

$$\bar{A}_j^{(+)} = \int dT_1 \int dT_2 \, P_J(T_1,T_2) f(W,T_1) \exp\left(-\frac{j\Delta}{T_2}\right) + N_j^{(+)}, \quad (2)$$

where $P_J(T_1, T_2)$ is the joint relaxation time distribution function and the integals are over the domain of the distribution function. As noted previously, experiments have shown that to within a good approximation, the joint distribution function in reservoir rocks has the form, $$P_J(T_1, T_2) = P(T_2)\delta(T_1 - \xi T_2), \quad (3)$$

where $\xi \sim 1.5$. That is, the $T_1$ and $T_2$ distributions are practically identical except for a constant scaling factor. Substitution of eq. (3) into (2) and performing the integration over $T_1$ leads to $$\bar{A}_j^{(+)} = \int_{T_{min}}^{T_{max}} dT_2 P(T_2) f(W,\xi T_2) \exp\left(-\frac{j\Delta}{T_2}\right) + N_j^{(+)}, \quad (4)$$

where for $A_j(\pm)$ expressed in volts, $P(T_2) \, dT_2$ is the signal amplitude in volts contributed by spectral components with transverse relaxation times in the interval $T_2$ to $T_2 + dT_2$. The domain of the function $P(T_2)$ is the closed interval $[T_{min}, T_{max}]$. The function $f(W, \xi T_2)$ accounts for the incomplete recovery of the longitudinal magnetization during the wait time W and is defined by, $$f(W,\xi T_2) = \left(1 - \exp\left(-\frac{W}{\xi T_2}\right)\right). \quad (5)$$

The integrals in eqs. (2) and (4) are the amplitudes of the transverse magnetization observed at the j-th echo and $N_j(+)$ is the thermal noise in the tool electronics.

Equation (4) is a Fredholm integral equation of the first kind for the distribution function $P(T_2)$. The solution of eq. (4) for $P(T_2)$ from the measured spin-echo signal-plus-noise amplitudes is the signal processing problem that must be confronted to obtain maximum information from the PNMT data. This type of problem represents an inverse problem of the type frequently encountered in remote sensing problems.[7] The relaxation time distribution is the central quantity of interest since essentially all of the petrophysical quantities of interest can be computed from this function.

Pre-Processing of Spin-Echo Data

As noted previously, the amplitudes of the spin-echoes are integrated over time windows and the integrated signals are recorded as $R_j$ and $X_j$ time series channels or waveforms. Each time series or CPMG$(+)$ is combined with its phase alternated pair CPMG$(-)$. The PAPS pairs are accumulated as the tool moves and then averaged and output into depth bins. Thus, in each depth bin the data typically consists of several hundred echoes $\bar{R}_j$ and $\bar{X}_j$ for $j = 1, 2, \ldots, J$ where J is the total number of echoes collected. Prior to applying the signal processing algorithm, the data in each depth bin are pre-processed. First, an estimate $\bar{\theta}$ of the signal phase is computed. Using $\bar{\theta}$ the $\bar{R}_j$ and $\bar{X}_j$ data are combined into two random time series $\bar{A}_j(+)$ and $\bar{A}_j(-)$. The random variables $\bar{A}_j(+)$ have the statistical properties of the phase coherent signal-plus-noise and are used to estimate the relaxation time distribution (i.e., by solving a discretized version of eq. (4)). The random variables $\bar{A}_j(-)$ have the statistical properties of the noise and are used to estimate the rms noise, $\sqrt{\psi}$, on a single echo of the PAPs pairs in each depth bin. In each depth bin the number of PAPs pairs accumulated and averaged depends on the pulse sequence parameters and the logging speed.

Statistical Properties of the Noise

The spin-echo in-phase and quadrature amplitudes can be written in the form, $$\bar{R}_j = S_j \cos\theta + N_j^{(c)}, \quad (6)$$

$$\bar{X}_j = S_j \sin\theta + N_j^{(s)}, \quad (7)$$

where $\theta$ is the signal phase and $S_j$ is the signal. $N_j^{(c)}$ and $N_j^{(s)}$ are thermal noise voltage fluctuations in the R and X receiver channels, respectively. The thermal noise fluctuations are uncorrelated, zero mean Gaussian random variables with the following statistical properties:

$$\{N_j^{(c)}\} = \{N_j^{(s)}\} = 0, \quad (8a)$$

$$\{N_j^{(c)} N_k^{(s)}\} = 0, \quad (8b)$$

$$\{N_j^{(c)} N_k^{(c)}\} = \{N_j^{(s)} N_k^{(s)}\} = \delta_{j,k}\psi. \quad (8c)$$

The angular brackets are used to denote statistical or ensemble averages and $\delta_{j,k}$ is the Kronecker delta function. Note that thermal noise fluctuations are a time translationally invariant stochastic process. Therefore it follows from the ergodic theorem that statistical averages can be replaced by time averages. In eq. (8c), $\psi$ is the noise variance on a single echo.

Signal Phase Estimator

An unbiased estimator $\bar{\theta}$ of the signal phase is computed from the in-phase and quadrature amplitudes, $$\bar{\theta} = \arctan\left[\frac{\sum_{j=1}^{J} \bar{X}_j}{\sum_{j=1}^{J} \bar{R}_j}\right], \quad (9)$$

To compute the mean and variance of $\bar{\theta}$, sum eqs. (6) and (7) over all echoes, i.e., $$\sum_{j=1}^{J} \bar{R}_j = \sum_{j=1}^{J} S_j \cos\theta + \sum_{j=1}^{J} N_j^{(c)}, \quad (10)$$

and, $$\sum_{j=1}^{J} \bar{X}_j = \sum_{j=1}^{J} S_j \sin\theta + \sum_{j=1}^{J} N_j^{(s)}, \quad (11)$$

from which it follows that, $$\cos\bar{\theta} = \cos\theta + \frac{\sum_{j=1}^{J} N_j^{(c)}}{\sum_{j=1}^{J} S_j}, \quad (12)$$

and, $$\sin\bar{\theta} = \sin\theta + \frac{\sum_{j=1}^{J} N_j^{(s)}}{\sum_{j=1}^{J} S_j}, \quad (13)$$

where I have defined, $$\cos\bar{\theta} = \frac{\sum_{j=1}^{J} \bar{R}_j}{\sum_{j=1}^{J} S_j}, \quad (14)$$

and, $$\sin\bar{\theta} = \frac{\sum_{j=1}^{J} \bar{X}_j}{\sum_{j=1}^{J} S_j}. \quad (15)$$

Combining eqs. (12) and (13) one finds to lowest order in the noise fluctuations that, $$\tan\bar{\theta} - \tan\theta \simeq \left[ \frac{\sum_{j=1}^{J} N_j^{(s)}}{\sum_{j=1}^{J} S_j \cos\theta} - \frac{\sum_{j=1}^{J} N_j^{(c)} \sin\theta}{\sum_{j=1}^{J} S_j \cos^2\theta} \right], \quad (16)$$

from which it follows that $$\bar{\theta} \simeq \theta + \frac{\sum_{j=1}^{J} N_j^{(s)} \cos\theta}{\sum_{j=1}^{J} S_j} - \frac{\sum_{j=1}^{J} N_j^{(c)} \sin\theta}{\sum_{j=1}^{J} S_j}, \quad (17)$$

where in obtaining the above equation I have used the result, $$\tan\bar{\theta} - \tan\theta \simeq \frac{(\bar{\theta} - \theta)}{\cos^2\theta}, \quad (18)$$

which is valid for $\bar{\theta} \simeq \theta$. It follows easily from eq. (17) and the statistical properties of the noise that, $$\{\bar{\theta}\} = \theta, \quad (19)$$

so that $\bar{\theta}$ is an unbiased estimator of the signal phase $\theta$. One also finds using the noise properties that, $$<\bar{\theta}^2> = \theta^2 + \frac{\psi}{\left(\sum_{j=1}^{J} S_j\right)^2}. \quad (20)$$

Finally, it follows from eqs. (19) and (20) that the variance in the phase estimator $\bar{\theta}$ is given by, $$\sigma^2(\bar{\theta}) = \frac{\psi}{\left(\sum_{j=1}^{J} S_j\right)^2}. \quad (21)$$

It should be noted that the phase estimator $\bar{\theta}$ is sensible provided that the signal-to-noise ratio is not too small. In practice, the signal phase is found to be relatively constant in zones with porosities greater than a few p.u. and exhibits random fluctuations in zones with no appreciable signal. It is a useful tool diagnostic since it should not vary with the formation and should be relatively constant in porous zones during a logging run.

Computation of $\bar{A}_j^{(+)}$ and $\bar{A}_j^{(-)}$

Using $\bar{\theta}$, it is convenient to construct two random time series from the $\bar{R}_j$ and $\bar{X}_j$. These are the signal-plus-noise amplitudes $\bar{A}_j^{(+)}$ introduced in eq. (2) and $\bar{A}_j^{(-)}$ which can be used to estimate $\psi$ from the data. These random time series are defined by, $$\bar{A}_j^{(+)} = \bar{R}_j \cos\bar{\theta} + \bar{X}_j \sin\bar{\theta}, \quad (22)$$

and $$\bar{A}_j^{(-)} = \bar{R}_j \sin\bar{\theta} - \bar{X}_j \cos\bar{\theta}. \quad (23)$$

The rationale for introducing $\bar{A}_j^{(+)}$ is that it has the statistical properties of a phase coherent signal. The above pair of equations has a simple vectorial interpretation, e.g., in eq. (22) the two terms on the right are the projections of the R and X components along the total signal whereas the terms in eq. (23) are projections perpendicular to the total signal. To calculate its expectation value first note that, $$\bar{A}_j^{(+)} = S_j \cos(\theta - \bar{\theta}) + N_j^{(+)} \simeq S_j + N_j^{(+)}, \quad (24)$$

where I have used eqs. (6), (7) and (22) and defined, $$N_j^{(+)} = N_j^{(c)} \cos\bar{\theta} + N_j^{(s)} \sin\bar{\theta}. \quad (25)$$

I have dropped terms in eq. (24) of order $(\bar{\theta} - \theta)^2$ which are assumed to be negligible. The expectation value of eq. (24) is obtained from the statistical properties of the noise. i.e., eqs. (8).

$$\{\bar{A}_j^{(+)}\} \simeq S_j. \quad (26)$$

One also finds that, $$\{(\bar{A}_j^{(+)})^2\} \simeq S_j^2 + \psi, \quad (27)$$

from which it follows that the variance in $\bar{A}_j^{(+)}$ is $\psi$. I shall make use of these results in the development of the algorithm for computing the spectral distribution function. Next it is shown that $\bar{A}_j^{(-)}$ has the properties of the noise. Substituting eqs. (6), (7) into (23) one finds that, $$\bar{A}_j^{(-)} = S_j \sin(\theta - \bar{\theta}) + N_j^{(-)} \simeq N_j^{(-)}, \quad (28)$$

where $$N_j^{(-)} = N_j^{(c)} \sin\bar{\theta} - N_j^{(s)} \cos\bar{\theta}. \quad (29)$$

Using the statistical properties of the noise one finds that, $$\{\overline{A}_j^{(-)}\} = 0, \quad (30)$$

and, $$\{(\overline{A}_j^{(-)})^2\} = \psi, \quad (31)$$

from which it follows that the variance in $\overline{A}_j^{(-)}$ is $\psi$. Thus, as noted previously, the random time series for $\overline{A}_j^{(-)}$ can be used to estimate the rms noise $\sqrt{\psi}$.

Spectral Decomposition Algorithm

Discretization of the Signal

First, the signal $S_j$ which is given by the integral in eq. (4) is discretized, i.e., $$\overline{A}_j^{(+)} = \sum_{l=1}^{N_o} a_l f_l \exp\left[-\frac{t_j}{T_{2,l}}\right] + N_j^{(+)}, \quad (32)$$

where it is assumed that there are $N_s$ components (i.e., basis functions) in the spectrum with relaxation times given by, $$T_{2,l} = T_{min}\left(\frac{T_{max}}{T_{min}}\right)^{\frac{l-1}{N_o-1}}, \quad (33)$$

for $l = 1, 2, \ldots, N_s$. Note that the $T_{2,l}$ are equally spaced on a logarithmic scale. In eq. (32), I have defined the polarization functions, $$f_l = \left(1 - \exp\left(-\frac{W}{\xi T_{2,l}}\right)\right). \quad (34)$$

The signal processing problem therefore becomes the determination of the $N_s$ spectral amplitudes $a_l = P(T_{2,l})\delta_l$ where $\delta_l = (T_{2,l+1} - T_{2,l-1})/2$.

Data Compression

In this section, the data $\overline{A}_j^{(+)}$ are reduced by introducing sums of echoes over time windows. As noted earlier, the different windows have different sensitivities to the various components of the spectrum. Consider $N_w$ non-overlapping windows. Define the window sum, $\overline{I}_{m,m+1}$, over $(N_{m+1} - N_m + \delta_{m,1})$ echoes in the m-th window, i.e., $$\overline{I}_{m,m+1} = \sum_{j=N_m+\rho_m}^{N_{m+1}} \overline{A}_j^{(+)}, \quad (35)$$

where $\rho_m = (1 - \delta_{m,1})$ for $m = 1, 2, \ldots N_w$ and $\delta_{m,1}$ is the familiar Kronecker delta function (e.g., equals 1 for $m=1$ and 0 otherwise). Here $(N_m + \rho_m)$ and $N_{m+1}$ are the echo numbers (i.e., endpoints) of the m-th window. More explicitly, for the first window $$\overline{I}_{1,2} = \sum_{j=N_1}^{N_2} \overline{A}_j^{(+)},$$

where $N_1$ and $N_2$ are the echo numbers of the endpoints of the first window. For the second window, $$\overline{I}_{2,3} = \sum_{j=N_2+1}^{N_3} \overline{A}_j^{(+)},$$

and, in general, for the n-th window where $n > 1$, $$\overline{I}_{n,n+1} = \sum_{j=N_n+1}^{N_{n+1}} \overline{A}_j^{(+)}.$$

Recalling eq. (32), one can write (35) in the form, $$\overline{I}_{m,m+1} = \sum_{l=1}^{N_o} a_l f_l F_{m,m+1}(T_{2,l}, N_m, N_{m+1}, \Delta) + \overline{N}_{m,m+1}, \quad (36)$$

where I have defined window spectral sensitivity functions $F_{m,m+1}$ given by geometric series, i.e., $$F_{m,m+1}(T_{2,l}, N_m, N_{m+1}, \Delta) = \sum_{j=N_m+\rho_m}^{N_{m+1}} \exp\left[-\frac{j\Delta}{T_{2,l}}\right] \quad (37)$$

and also defined the sums over noise, $$\overline{N}_{m,m+1} = \sum_{j=N_m+\rho_m}^{N_{m+1}} N_j^{(+)}. \quad (38)$$

In each window the set of sensitivity functions defined above for $l = 1, \ldots N_s$ provide the relative sensitivity of each window to the different components in the spectrum.

Performing the summation in eq. (37), one finds that the sensitivity functions can be expressed in a form convenient for computation, i.e., $$F_{m,m+1}(x_l, N_m, N_{m+1}) = \quad (39)$$

$$\frac{\exp(-x_l)}{(1 - \exp(-x_l))}[\exp[-(N_m - \delta_{m,1})x_l] - \exp[-N_{m+1}x_l]],$$

where $x_l = \Delta/T_{2,l}$. In practice, it has been found that for PNMT log data that usually 3 windows are sufficient (i.e., the log outputs are not altered by adding more windows). Likewise for continuous logging it has been found that $N_s = 8$ is sufficient. This is discussed further in a section that examines the statistical uncertainties in the log outputs.

Statistical Properties of Window Sums

The statistical properties of the reduced set of random variables $I_{m,m+1}$ are determined from the known statistical properties of the noise. One finds from eq. (36) that their expectation values are given by, $$<\overline{I}_{m,m+1}> = \sum_{l=1}^{N_o} a_l f_l F_{m,m+1}(T_{2,l}, N_m, N_{m+1}, \Delta) \equiv I_{m,m+1}\{a_l\}, \quad (40)$$

where the curly brackets on the right are used to indicate that the expectation value is a functional (i.e., a scalar whose value depends on a function) of the spectral amplitudes. The above expression has a simple physical interpretation, i.e., the expected value of the sum of the signal over the m-th window is the weighted sum of the sensitivity functions of the various spectral components each weighted by its amplitude. The variances in the window sums are easily calculated. One finds that, $$\sigma^2(\bar{I}_{m,m+1}) = \psi(N_{m+1} - N_m + \delta_{m,1}) \equiv \psi \sigma_{m,m+1}^2. \quad (41)$$

Here $\psi$ is the variance of the noise in a single echo which is the same for all echoes. The variance of the window sum in the above equation is simply the number of echoes in the window times the variance in a single echo. Note that this result is evident from elementary statistics since the variance in a sum of uncorrelated random variables is simply the sum of the variances. For non-overlapping windows the window sums over different windows are uncorrelated, i.e., $$<\delta \bar{I}_{m,m+1} \delta \bar{I}_{m,m+1}> = \delta_{m,m'} \psi \sigma_{m,m+1}^2, \quad (41a)$$

where from eq. (36), $\delta \bar{I}_{m,m+1} = \bar{N}_{m,m+1}$.

Spectral Estimation

The window sums defined in eq. (35) are independent Gaussian random variables with expectation values and variances given by eqs. (40) and (41), respectively. The logarithm of the likelihood function for the $N_w$ window sums is given by, $$-\ln L = \sum_{m=1}^{N_\omega} \frac{(\bar{I}_{m,m+1} - I_{m,m+1}\{a_l\})^2}{2\psi[N_{m+1} - N_m + \delta_{m,1}]} + \frac{\gamma}{2\psi} \sum_{l=1}^{N_c} a_l^2, \quad (42)$$

where the expected values $<\bar{I}_{m,m+1}> \equiv I_{m,m+1}\{a_l\}$ were defined earlier and are functions of the spectral parameters which we want to estimate. The last term is a phenomenological regularization term introduced to prevent noise amplification artifacts. It is a penalty constraint that prevents the $L_2$ norm of the amplitudes from becoming too large. The $L_2$ regularization is commonly employed but other criteria can be imposed. The spectral amplitudes are relatively insensitive to the dimensionless parameter $\gamma$. A value $\gamma \simeq 5$ is usually used for PNMT log data. How to best choose $\gamma$ is not a trivial question. The best fit to the data occurs if $\gamma = 0$, however, the solution is not stable. It would be the best solution in the absence of noise. In the presence of noise, the squared residuals of the fit of the data in each window should be equal to the variance in the window sums in eq. (41). This represents the best fit based on the statistics of the model. Increasing $\gamma$ reduces the variance in the estimates but can lead to solutions that do not fit the data if $\gamma$ is too large. An algorithm for a priori estimation of an "optimal" $\gamma$ determined at each depth from the data is developed in Appendix A. The spectral amplitudes $\{a_l\}$ are determined by minimization of eq. (42) subject to a positivity constraint. The estimation is extremely fast on a computer as only a few (e.g., 3) windows are needed. The computation time is essentially independent of the number of echoes.

The above algorithm leads to a tremendous data reduction since the spectrum is obtained from only a few random variables instead of hundreds or thousands of echoes. This huge data reduction has obvious potential benefits for efficient data acquisition and storage. A set (e.g., 10–100) of window sums can be rapidly computed downhole and transmitted uphole for processing. This set can be combined into gates for uphole processing. This leads to a substantial reduction in PNMT telemetry requirements which is important for commercial tools run in combination. Downhole preprocessing can be used to assess data quality and flags established for sending all of the echoes uphole if necessary.

Total, Free and Bound Fluid Porosities

The spectral analysis described above leads immediately to logs of total, bound and free fluid porosities and mean transverse spin relaxation time. The total NMR porosity $\phi_{nmr}$ can be computed by integration of the distribution function $P(T_2)$ defined in eq. (4), i.e., $$\phi_{nmr} = K_{tool} \int_{T_{min}}^{T_{max}} dT_2 P(T_2) = K_{tool} \sum_{l=1}^{N_c} a_l, \quad (43)$$

where $K_{tool}$ is a tool constant for converting volts to porosity. Similarly, the free-fluid porosity is given by, $$\phi_f = K_{tool} \sum_{l=N_c}^{N_c} a_l + \Delta \phi, \quad (44)$$

where for the free fluid porosity (denoted by UBF on PNMT logs), the summation is over a subset of components, $l = N_c, N_c+1, \ldots, N_s$ for which $T_{2,l} \geq T_c$. Centrifuge experiments by Straley, et al[8] have found that in many sandstones $T_c \simeq 33$ milliseconds. The bound-fluid porosity is simply given by $\phi_{bf} = \phi_t - \phi_f$. The term $\Delta \phi$ is a small correction which accounts for the fact that the cut-off $T_c$ does not lie on the endpoint of the free fluid integration interval. An analytic expression is derived in Appendix C for the $\Delta \phi$ correction. Note that this correction does not affect $\phi_t$, i.e., only the partitioning of the free and bound fluid porosities.

Distributions And Mean Relaxation Times

The porosity distribution function $P(T_3)$ is with respect to $T_2$. For displaying maps of porosity distributions versus relaxation time, it is useful to define a logarithmic distribution $P_a(\log T_2)$ since the relaxation times span several decades. In terms of the logarithmic distribution function, $$\phi_{nmr} = K_{tool} \int_{\log T_{min}}^{\log T_{max}} d(\log T_2) P_a(\log T_2), \quad (45)$$

where $K_{tool} P_a(\log T_2) d(\log T_2)$ is the porosity in the interval $[\log T_2, \log T_2 + d(\log T_2)]$. The distributions with respect to $T_2$ and $\log T_2$ are related, i.e., $$P(T_2) = \frac{c P_a(\log T_2)}{T_2}, \quad (46)$$

with $c = (\ln 10)^{-1}$ as can be shown using eqs. (43) and (45). Using the discretization of $P(T_2)$ introduced earlier, the discretized distribution with respect to the $T_{2,l}$ defined in eq. (33) is given by, $$P(T_{2,l}) = \frac{a_l}{\delta_l}, \quad (47)$$

with $\delta_l = (T_{2,l+1} - T_{2,l-1})/2$. Using eq. (33), it follows from simple algebra that, $$\delta_l = \frac{T_{2,l}(r^2 - 1)}{2r}, \quad (48)$$

where I have defined, $$r = \left(\frac{T_{max}}{T_{min}}\right)^{\frac{1}{N_c-1}}. \tag{49}$$

Combining eqs. (46)–(48), one finds that, $$P_a(\log T_{2,l}) = \frac{2a_l r}{c(r^2-1)}. \tag{50}$$

Note that to within a constant factor, independent of l, the logarithmic distribution is proportional to the amplitude distribution $\{a_l\}$.

The main results concerning distributions are eqs. (47) and (50). In summary, to display the distribution $P(T_2)$, use eq. (47) to compute $P(T_{2,l})$ and plot it versus $T_{2,l}$ on a linear scale. To display, the logarithmic distribution use eq. (50) to compute $P_a(\log T_{2,l})$ and plot it versus $T_{2,l}$ on a logarithmic scale. More simply, plot the $\{a_l\}$ distribution on a logarithmic $T_{2,l}$ scale to obtain the logarithmic distribution to within a constant scale factor.

A mean relaxation time $\overline{T}_2$ can be defined for the distribution $P(T_2)$. That is, $$\overline{T}_2 = \frac{\int_{T_{min}}^{T_{max}} dT_2 P(T_2) T_2}{\int_{T_{min}}^{T_{max}} dT_2 P(T_2)}, \tag{51}$$

or in discretized form, $$\overline{T}_2 = \frac{\sum_{l=1}^{N_c} a_l T_{2,l}}{\sum_{l=1}^{N_c} a_l}. \tag{52}$$

Analagously, a logarithmic mean relaxation time $\overline{T}_{2,log}$ can be defined. First, one defines a mean logarithm m for the $P_a(\log T_2)$ distribution, i.e., $$\overline{m} = \frac{\int_{\log T_{min}}^{\log T_{max}} d(\log T_2) P_a(\log T_2) \log T_2}{\int_{\log T_{min}}^{\log T_{max}} d(\log T_2) P_a(\log T_2)}, \tag{53}$$

or in discretized form, $$\overline{m} = \frac{\sum_{l=1}^{N_c} \delta\, P_a(\log T_{2,l}) \log T_{2,l}}{\sum_{l=1}^{N_c} \delta\, P_a(\log T_{2,l})} = \frac{\sum_{l=1}^{N_c} a_l \log T_{2,l}}{\sum_{l=1}^{N_c} a_l}. \tag{54}$$

Note that on a logarithmic scale the spacings, $\delta = \log T_{2,l+1} - \log T_{2,l} = (N_s-1)^{-1}\log[T_{max}/T_{min}]$, are equal and therefore independent of l. The last equality in the above equation follows from the result in eq. (50). The logarithmic mean relaxation time $T_{2,log}$ is obtained by exponentiation, $$\overline{T}_{2,log} = 10^{\overline{m}}. \tag{55}$$

The logarithmic mean relaxation times $\overline{T}_{2,log}$ and porosities $\phi_{nmr}$ are used as inputs into empirically derived equations to provide estimates of permeabilities.

Variances In The Porosity Estimators

The variances in the porosity estimators $\hat{\phi}_{nmr}$, $\hat{\phi}_f$ and $\hat{\phi}_{bf}$ are computed from the covariance matrix $C_{l,k}$. The porosity estimators are obtained from estimates of the spectral amplitudes, i.e., $$\hat{\phi}_{nmr} = K_{tool} \sum_{l=1}^{N_c} \hat{a}_l, \tag{56}$$

where the hat is used to differentiate the estimators from the true quantities (e.g., in eqs. (43)–(44) true porosities and spectral amplitudes are indicated). The variance $\sigma^2(\hat{\phi}_{nmr})$ is by definition, $$\sigma^2(\hat{\phi}_{nmr}) \equiv \langle \hat{\phi}_{nmr}^2 \rangle - (\langle \hat{\phi}_{nmr} \rangle)^2, \tag{57}$$

or explicitly by, $$\sigma^2(\hat{\phi}_{nmr}) = K_{tool}^2 \sum_{l=1}^{N_c} \sum_{k=1}^{N_c} C_{l,k}, \tag{58}$$

where the parameter-parameter covariance matrix, $$C_{l,k} = \langle \delta \overline{a}_l \delta \overline{a}_k \rangle, \tag{59}$$

has been introduced. The angular brackets denote statistical averages and the fluctuations $\delta \overline{a}_k$ are defined by, $$\delta \overline{a}_k = \overline{a}_k - \langle \overline{a}_k \rangle. \tag{60}$$

Note the covariance matrix is symmetric and its diagonal elements are the variances in the amplitudes, i.e., $\sigma^2(a_l)$. In general, the fluctuations in the amplitude estimates are correlated and therefore the off-diagonal elements of $C_{l,k}$ are non-zero. The derivation of the variances in the free and bound fluid porosities is analogous to the derivation of eq. (58). One finds, for example, that $$\sigma^2(\hat{\phi}_j) = K_{tool}^2 \sum_{l=N_c}^{N_c} \sum_{k=N_c}^{N_c} C_{l,k}. \tag{61}$$

where $N_c$ is defined in eq. (44). In order to apply eqs. (58) and (61), one needs to compute the covariance matrix. An approximation for the covariance matrix will be derived in a subsequent section. First, however, an approximate calculation of the variance in the logarithmic mean relaxation time is presented.

Variance In The Logarithmic Mean Relaxation Times

In this section an approximate formula for the variance in $\overline{T}_{2,log}$ is derived. Recalling eqs. (54) and (55) one finds that, $$\overline{T}_{2,log}\{a_l\} = \exp\left[\frac{c \sum_l \overline{a}_l \ln T_{2,l}}{\sum_l a_l}\right], \tag{62}$$

where the curly bracket on the left indicates that $\overline{T}_{2,log}$ is a functional of the amplitude estimates $a_l$. It is to be understood that the summations on the right are over the whole spectrum, i.e., $l=1,2,\ldots,N_s$. The constant $c = (\ln 10)^{-1}$. Expand $T_{2,log}$ in a Taylor's series about the expectation values of the amplitude estimates, i.e., $$\overline{T}_{2,log}\{\bar{a}_l\} = \overline{T}_{2,log}(<\bar{a}_l>) + \sum_{k=1}^{N_o}\left(\frac{\partial \overline{T}_{2,log}}{\partial \bar{a}_k}\right)\delta \bar{a}_k + \ldots \quad (63)$$

Note that in eq. (63), it has been assumed that the fluctuations are sufficiently small that terms of order $(\delta a_k)^2$ can be neglected. The derivatives on the right are, of course, evaluated at $<a_k>$. To proceed, another small fluctuation approximation, i.e., $<T_{2,log}> \cong T_{2,log}(<a_l>)$ is employed to obtain $$\sigma^2(\overline{T}_{2,log}) \equiv <(\delta \overline{T}_{2,log})^2> = \sum_{k=1}^{N_o}\sum_{l=1}^{N_o}\left(\frac{\partial \overline{T}_{2,log}}{\partial \bar{a}_k}\right)\left(\frac{\partial \overline{T}_{2,log}}{\partial \bar{a}_l}\right)C_{l,k}, \quad (64)$$

where, $\delta T_{2,log} \equiv (T_{2,log} - <T_{2,log}>)$, and eqs. (59) and (63) have been used. The partial derivatives can be evaluated explicitly using eq. (62). One finds after some simple algebra that the standard deviation, $$\sigma(\overline{T}_{2,log}) = \overline{T}_{2,log}\left[\sum_{l=1}^{N_o}\sum_{k=1}^{N_o} P_l P_k C_{l,k}\right]^{\frac{1}{2}}, \quad (65)$$

where I have defined the quantities, $$P_l = \frac{\delta}{(\Sigma_l <a_l>)^2}\sum_{k=1}^{N_o}<\bar{a}_k>(l-k), \quad (66)$$

where eq. (33) was used in obtaining the above result. Here $\delta$ is the $\overline{T}_{2,l}$ spacing on a logarithmic scale (e.g., see the remarks following eq. (54)). In actual computations, the expectation values in the above equations are replaced by the maximum likelihood estimates obtained by the minimization of eq. (42). The calculation of the variance in $\overline{T}_2$ can be derived by similar manipulations but is not given here. The notion of a relaxation time becomes meaningless whenever the signal is dominated by the noise. This occurs in low porosity (e.g., for $\phi_{nmr} \cong 1$ p.u.) formations and leads to random fluctuations in $\overline{T}_{2,log}$ usually occurring at long times since noise amplitude fluctuations are non-decaying. In these instances eq. (65) provides a useful criterion for "turning off" the $\overline{T}_{2,log}$ log curve. A criterion which has proven useful is to disallow the log curve if the factor multiplying $\overline{T}_{2,log}$ on the right side of eq. (65) exceeds unity.

Calculation of the Parameter-Parameter Covariance Matrix

An exact covariance matrix can be calculated for the algorithm. Using eqs. (A.1)–(A.3) and eq. (42), it is easy to prove that the parameter estimates are related to the "data" via the set of linear equations, $$\bar{a}_l = R_{l,m}\bar{I}_{m,m+1}, \quad (67)$$

for $l = 1, 2, \ldots, N_s$ and where the Einstein summation convention of summing over repeated indices is used in this section. In the above equation, I have defined the $N_s \times N_w$ matrix R, $$R_{l,m} = M_{l,k}^{-1}Q_{k,m}, \quad (68)$$

where the $N_s \times N_s$ matrix M is defined by, $$M_{l,k} = \sum_{m=1}^{N_\omega}\frac{f_k F_{m,m+1}(T_{2,k}) f_l F_{m,m+1}(T_{2,l})}{\sigma_{m,m+1}^2} + \gamma \delta_{k,l}. \quad (69)$$

and where the $N_s \times N_w$ matrix Q is defined by, $$Q_{k,m} = \frac{f_k F_{m,m+1}(T_{2,k})}{\sigma_{m,m+1}^2}, \quad (70)$$

where $\sigma_{m,m+1}^2$ is defined in eq. (41). Using the definition of the parameter-parameter covariance matrix in eq. (59) and eqs. (41) and (41a) one finds that, $$C_{l,k} = R_{l,m}\psi\sigma_{m,m+1}^2 R_{m,k}^t. \quad (71)$$

The parameter-parameter covariance matrix in eq. (71) can be used with eqs. (58), (61) and with an analogous equation for $\sigma^2(\bar{\phi}_{bf})$ to study the standard deviations in $\bar{\phi}_t$, $\bar{\phi}_f$ and $\bar{\phi}_{bf}$ for various pulse and processing parameters. Some of these results are shown in FIGS. 17–20. The PNMT logs from repeat runs generally agree very well with the standard deviations computed from the covariance matrix. It should be noted, however, that log repeatability can be affected by many factors other than statistical fluctuations (e.g., hole conditions). Therefore the uncertainties computed using eq. (71) and displayed on the logs may in some cases be optimistic compared to the log uncertainties estimated from statistical analysis of repeat runs. A proof that the matrix M is positive definite and therefore has an inverse is given in Appendix B.

Processing Example From a PNMT Field Test

The algorithm described above has been used to process log data from five Schlumberger client wells logged to date. A flowchart illustrating the various steps in the implementation of the algorithm is shown in FIG. 13.

A detailed discussion of the field examples is beyond the scope of this report. Here, it will suffice to show a short section of processed continuous PNMT log data and the analysis of station data acquired at several depths within the interval. The log data shown was acquired with the PNMT tool moving at 150 ft/hour. FIG. 16 shows a section of log from a well in Texas. The section shown contains a non-hydrocarbon bearing thinly bedded sand/shale sequence. In Track 1, a color map of signal versus relaxation time ($T_2$) plotted on a logarithmic scale is shown. The magnitude of the signal is proportional to the intensity of the color and in this example, the $T_2$ range is from 1 ms to 1500 ms. The red curve in Track 1 is the logarithmic mean ($T_{2,log}$) of the distribution. In Track 2, the rms noise estimate ($\sqrt{\psi}$) in volts, the estimated standard deviations in the total and free-fluid porosities, and the signal phase estimate ($\bar{\theta}$) in degrees are displayed. Note that $\bar{\theta}$ is essentially constant, as expected, except at depths with low porosities (i.e., low signals) where the phase estimator is dominated by random noise. In Track 3, the total and free-fluid porosity estimates are displayed.

Several station stop measurements were made in the logged interval. At station stops, the tool acquires data for several minutes. The data is averaged to reduce the noise so that the quality of the station data is significantly better than the continuous data. The signal processing of the station data is the same as for the continuous data.

Figure 21:
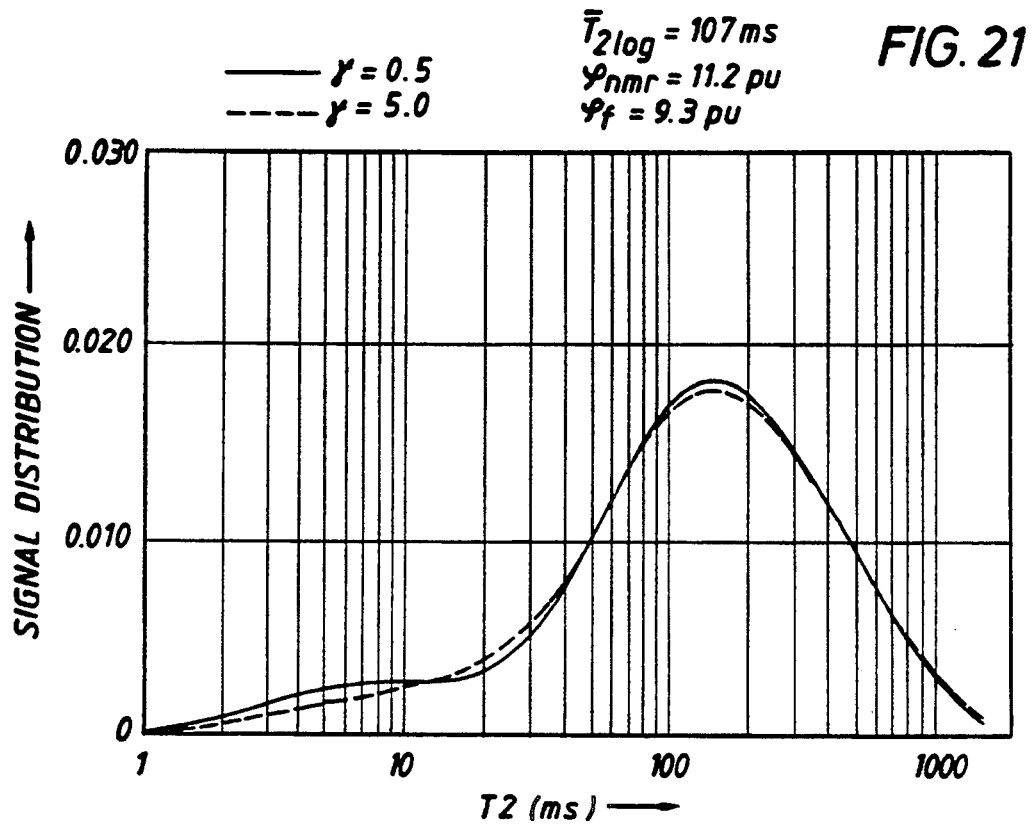
FIG. 21 illustrates a signal distribution computed from station data at 1100 ft for two values of gamma differing by an order of magnitude.

In FIG. 21, the signal distribution (analogous to the color map shown in FIG. 16) versus $T_2$ is shown for a station stop at 1100 ft. Recall that the area under the signal distribution curve is proportional to porosity. Comparing FIG. 21 with the continuous log observe that the total NMR porosity ($\phi_{nmr}$), free-fluid porosity ($\phi_f$), and logarithmic mean relaxtion time ($\overline{T}_{2,log}$) computed from the station stop data agree well with the continuous log values. The values shown were computed with a regularization parameter, $\gamma = 5.0$, as was the continuous log. It should be noted, that it has been found that estimates of $\phi_{nmr}$, $\phi_f$ and $\overline{T}_{2,log}$ depend only weakly on the regularization parameter. For example, changing $\gamma$ by an order of magnitude usually results in porosity variations of less than $\pm 0.5$ pu. The detailed shape of the signal distribution, however, can be changed significantly in some cases by varying the regularization parameter. This is a consequence of the fact that there are infinitely many solutions which will fit the data. Decreasing $\gamma$ reduces the fit error but can increase the norm of the solution vector.

In FIG. 21, the two signal distributions plotted correspond to two very different values of the regularization parameter. Note that there is practically no difference in the two distributions. Both distributions fit the data to within the noise and have comparable norms. Therefore both solutions are mathematically acceptable.

Figure 22:
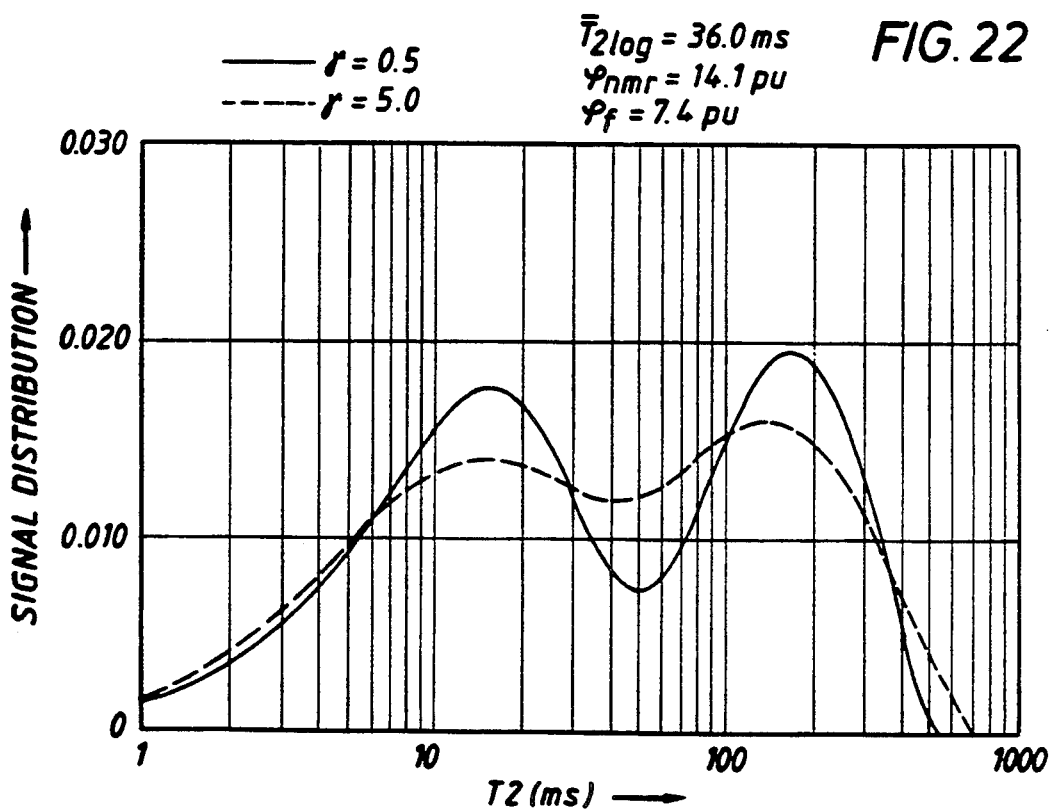
FIG. 22 illustrates a signal distribution at 1125 ft exhibiting a two peak structure reflecting two disparate pore size distributions.

In FIG. 22, results from a station stop at 1125 ft are displayed. The two signal distributions corresponding to values of $\gamma$ differing by an order of magnitude are qualitatively similar. The distribution computed with $\gamma = 0.5$ amplifies the two peak structure already apparent in the distribution computed using $\gamma = 5.0$. In this example, the two peaks are probably due to signal contributions from two disparate pore distributions in the thinly bedded heterogeneous reservoir at 1125 ft as indicated on the FMS image (not shown here). In oil reservoirs, where the formation is relatively homogeneous over the length of the PNMT tool aperture, separate oil and water signal peaks can be identified in the signal distribution.

Figure 23:
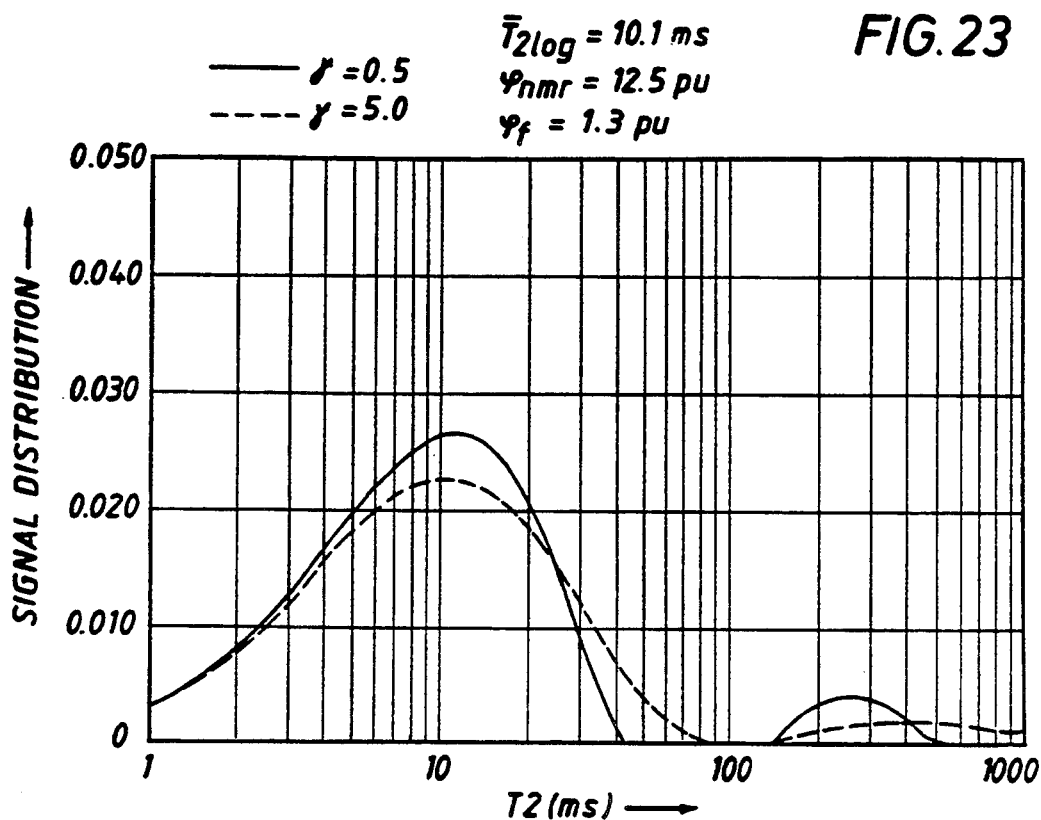
FIG. 23 illustrates a signal distribution at 1148 ft indicating a relatively poor reservoir quality rock.

In FIG. 23, results from a station stop at 1148 ft are shown. Note that, the continuous log outputs agree well with those obtained by processing the station data. Note that, the reservoir quality at this depth is poor compared to that at the previous two stations as evidenced by almost all of the signal being associated with bound fluid porosity.

Figure 24:
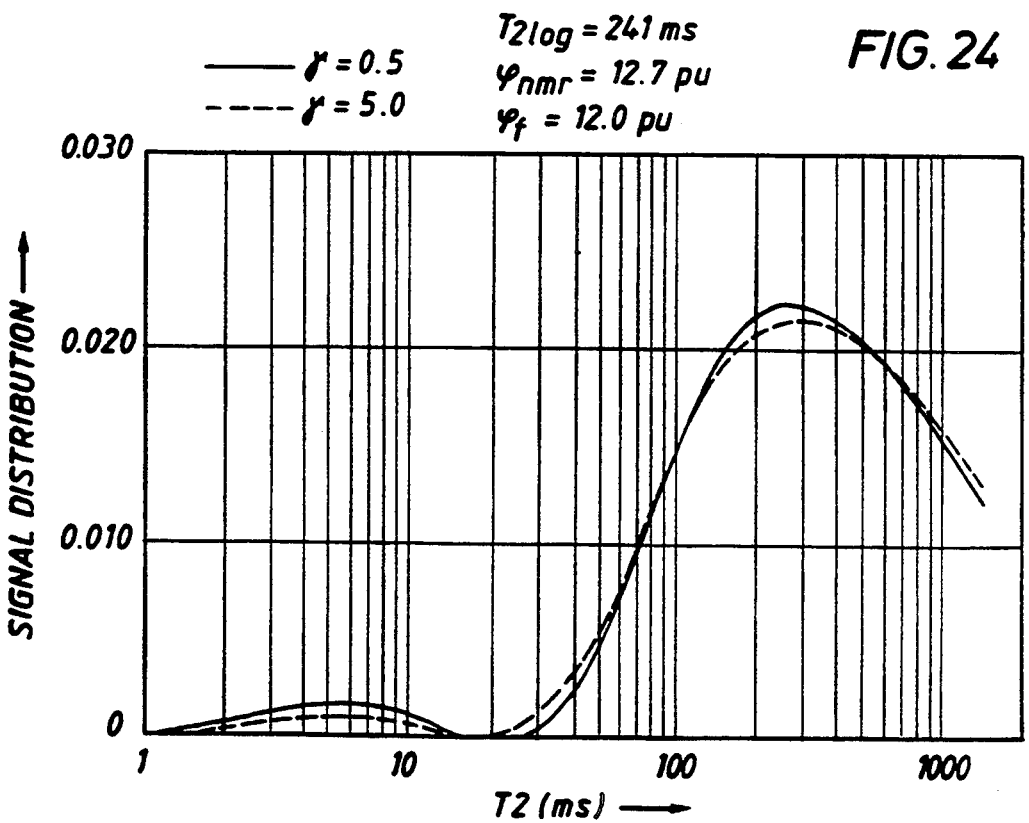
FIG. 24 illustrates a signal distribution at 1200 ft indicating a relatively good quality permeable reservoir rock.
Figure 25:
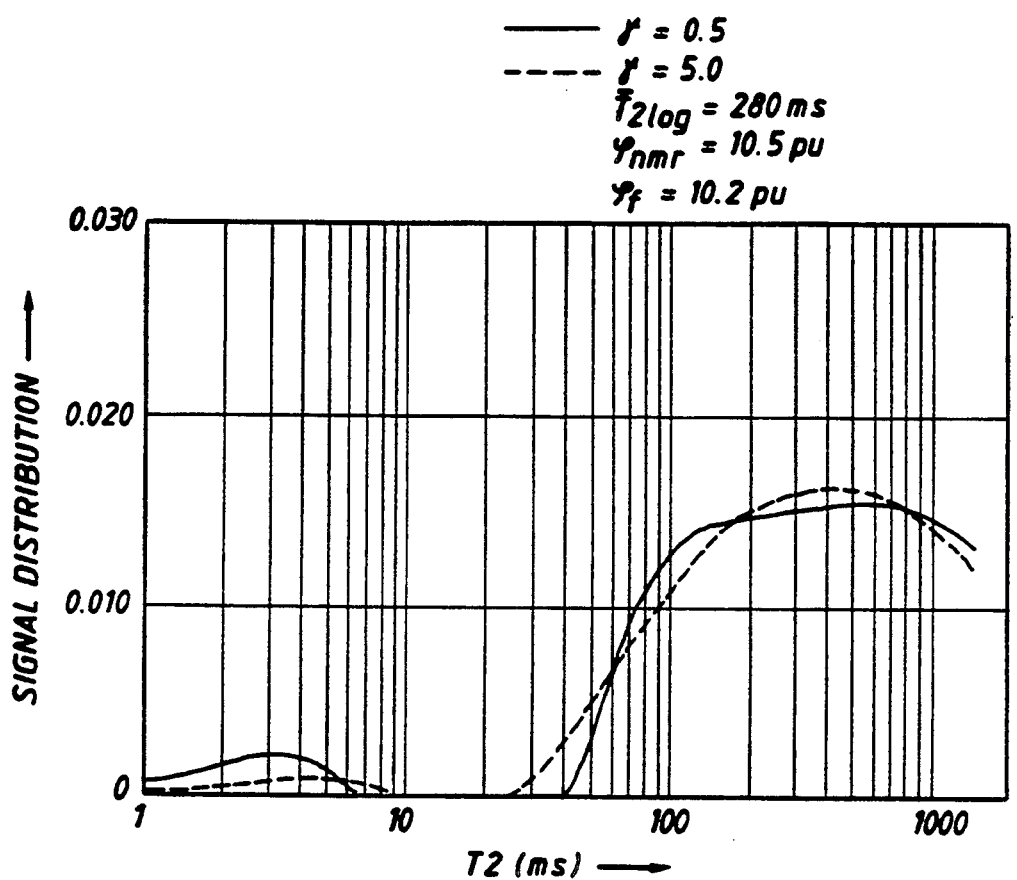
FIG. 25 illustrates a signal distribution at 1229 ft indicating essentially no bound fluid, and a long relaxation time.

In FIGS. 24 and 25 the station stops at 1200 ft and 1229 ft are shown. These distributions, reveal relatively high permeability reservoir rock at these depths. The long relaxation times are indicative of large pore and, pore surfaces free of iron or other magnetic material.

References

The following references support the specification teachings.

1. Sezginer, A., Kleinberg, R. L., Fukuhara, A., and Latour, L. L., "Very Rapid Measurement of Nuclear Magnetic Resonance Spin-Lattice Relaxation Time and Spin-Spin Relaxation Time," J. of Magnetic Resonance, v. 92, 504–527 (1992).
2. Kleinberg, R. L., Sezginer, A., Griffin, D. D., and Fukuhara, M., "Novel NMR Apparatus for Investigating an External Sample," J. of Magnetic Resonance, v. 97, 466–485 (1992).
3. Gallegos, D. P. and Smith, D. M., "A NMR Technique for the Analysis of Pore Structure: Determination of Continuous Pore Size Distributions," J. of Colloid and Interface Science, v. 122, No. 1, pp. 143–153, March, 1988.
4. Brown, R. J. S., Borgia, G. C., Fantazzini, P., and Mesini, E., "Problems In Identifying Multimodal Distributions Of Relaxation Times For NMR In Porous Media," Magnetic Resonance Imaging, Vol. 9, pp. 687–693 (1991).
5. Kenyon, W. E., Howard, J. J., Sezginer, A., Straley, C., Matteson, A., Horkowitz, R., and Erlich, R., "Pore-size Distribution and NMR in Microporous Cherty Sandstones" Trans. of the SPWLA of the 30th Ann. Logging Symp., Paper LL, Jun. 11–14, 1989.
6. Latour, L. L., Kleinberg, R. L. and A. Sezginer, "Nuclear Magnetic Resonance Properties of Rocks at Elevated Temperatures," J. of Colloid and Interface Science, v. 150, 535 (1992).
7. Twomey, S., "Introduction To The Mathematics of Inversion In Remote Sensing And Indirect Measurements," published by Elsevier Scientific Publishing Company, 1977.
8. Straley, C., Morriss, C. E., Kenyon, W. E., and Howard, J. J., "NMR in Partially Saturated Rocks: Laboratory Insights on Free Fluid Index and Comparison with Borehole Logs," Trans. of the SPWLA 32nd Ann. Logging Symp., Paper CC, Jun. 16–19, 1991.
9. Butler, J. P., Reeds, J. A. and Dawson, S. V., "Estimating Solutions of First Kind Integral Equations with Non-Negative Constraints and Optimal Smoothing," SIAM J. Numerical Anal., v. 18, no. 3, 381–397, 1981.

Appendix A: An Algorithm for Optimal Selection of $\gamma$

In this Appendix an algorithm for selection of an "optimal" regularization parameter $\gamma_{opt}$ is derived. A similar algorithm was derived by Butler, Reeds and Dawson[9] and has been used by Gallegos and Smith[3] to select the regularization parameter. The selection criterion for choosing $\gamma_{opt}$ is based on the notion that an optimal value of smoothing is obtained by minimizing the squared norm of the difference vector $\delta\bar{a} = \bar{a}_\gamma - \bar{a}_{true}$, where $\bar{a}_\gamma$ is the regularized solution and $a_{true}$ is the true distribution. Since $a_{true}$ is, of course unknown, a compromise is made by replacing $a_{true}$ by a hypothetical noise free solution a for which $\gamma = 0$. Although, the aforementioned criterion can be rigorously stated, assumptions must be made that introduce elements of empiricism into the algorithm. These elements are also present in other algorithms[9] and therefore the claims of optimality are somewhat subjective.

Maximum likelihood estimates of the $N_s$ spectral amplitudes $a_l$ are obtained by minimization of, $-\ln L$, in eq. (42). The equations to be solved are $$\frac{\partial \ln L}{\partial a_l} = 0, \qquad (A.1)$$

for $l = 1, 2, \ldots, N_s$. Substituting eq. (42) into (A.1) leads to the linear system of equations, $$\sum_{k=1}^{N_o} M_{l,k} a_k = d_l, \qquad (A.2)$$

where the symmetric matrix $M_{l,k}$ is defined in eq. (69) and the data vector $$d_l = \sum_{m=1}^{N_\omega} \frac{\bar{I}_{m,m+1} f_l F_{m,m+1}(T_2,l)}{\sigma^2_{m,m+1}}, \quad (A.3)$$

has been defined. The quantities $f_l$, $\bar{I}_{m,m+1}$ and $F_{m,m+1}(T_2,l)$ are defined in eqs. (34), (35) and (39), respectively, and $$\sigma\bar{}_{m,m+1} = N_{m+1} - N_m + \delta_{m,1}, \quad (A.4)$$

have been defined. The $\sigma_{m,m+1}^2$ are simply the number of echoes in the m-th window.

It is useful to write eq. (A.2) in an explicit matrix form, $$M\bar{a}_\gamma = \bar{d}, \quad (A.5)$$

and to also write the companion equation, $$M_0 \bar{a}^{(0)} = \bar{d}^{(0)}, \quad (A.6)$$

where $a_\gamma$ is a vector whose $N_s$ components are the spectral amplitudes for a regularization parameter $\gamma$, d is the data vector defined in eq. (A.3). The matrix $M_0$ is defined by the matrix equation, $$M = M_0 + \gamma I \quad (A.7)$$

where $I \in R^{N_s \times N_s}$ is the identity matrix. In (A.6), $a^{(0)}$ is the vector of spectral amplitudes corresponding to hypothetical noise free data and $a^{(0)}$ is the noise free data vector, i.e., $$\bar{d} = \bar{d}^{(0)} + \bar{n}, \quad (A.8)$$

where the noise vector n is defined by, $$n_l = \sum_{m=1}^{N_\omega} \frac{N_{m,m+1} f_l F_{m,m+1}(T_2,l)}{\sigma^2_{m,m+1}}, \quad (A.9)$$

where $N_{m,m+1}$ is defined in eq. (38).

It follows from the theory of matrices that the real symmetric matrix M can be diagonalized by an orthogonal transformation, i.e., $$M = UD_\gamma U^t, \quad (A.10)$$

where $U^t$ is the transpose of U where U is an $N_s \times N_s$ matrix whose columns are an orthonormal set of eigenvectors of M, i.e., the vectors $u_j$ satisfy the eigenvalue equation, $$M\bar{u}_j = \lambda_j(\gamma)\bar{u}_j, \quad (A.11)$$

and the othonormality conditions, $$\sum_{l=1}^{N_c} u_l^j u_l^j = \delta_{j,i}, \quad (A.12a)$$

or the matrix equivalent, $$U^t U = I. \quad (A.12b)$$

where $\lambda_j(\gamma)$ is the eigenvalue of M associated with eigenvector $\bar{u}_j$. The $N_s \times N_s$ matrix $D_\gamma$ in eq. (A.10) is a diagonal matrix with the eigenvalues $\lambda_j(\gamma)$ on the diagonal. The above equations result from the orthonormality of the columns of the matrix M. Note that the operator M does not have a null space, i.e., it is positive definite for $\gamma > 0$.

It can also be proven for orthogonal transformation square matrices like U that the rows are likewise orthonormal which leads to the equations, $$\sum_{l=1}^{N_c} u_j^l u_k^l = \delta_{j,k}, \quad (A.13a)$$

or its matrix equivalent, $$U^t = I. \quad (A.13b)$$

The operator $M_0$ has a non-trival null space because the rank (denoted by r) of $M_0$, i.e., the dimension of its non-null space is less than $N_s$. $M_0$ has reduced rank because the data are not independent. This is typical of most inversion problems and mathematically the problem is underdetermined (more unknowns than measurements). In mathematical terms, $$M_0 \bar{u}_j = \lambda_j(0)\bar{u}_j, \quad (A.14a)$$

for $j = 1, 2, \ldots, r$ where the eigenvalues can be ordered so that $\lambda_1(0) > \lambda_2(0) > \ldots > \lambda_r(0) > 0$. Also in the null space, $$M_0 \bar{u}_j = 0, \quad (A.14b)$$

for $j = r+1, \ldots, N_s$. The operator $M_0$ can be diagonalized in its non-null space by the transformation, $$M_0 = U_r D_0 U_r^t, \quad (A.15)$$

where $U_r$ is an $N_s \times r$ matrix whose columns are the eigenvectors $\bar{u}_j$ where $j = 1, 2, \ldots r$, and $D_0$ is a diagonal matrix with eigenvalues $\lambda_j(0)$ for $j = 1, 2, \ldots, r$ as diagonal elements.

It follows from (A.7) that the eigenvalues $\lambda_j(\gamma)$ of M are simply related to those of $M_0$, $$\lambda_j(\gamma) = \lambda_j(0) + \gamma. \quad (A.16)$$

To proceed, one uses the transformation (A.10) in eq. (A.5) to write, $$\bar{a}_{65} = M^{-1}\bar{d} = UD_\gamma^{-1}U^t\bar{d}, \quad (A.17)$$

and similarly using eq. (A.15) and (A.6), $$\bar{a}^{(0)} = M_0^{-1}\bar{d}^{(0)} = U_r D_0^{-1} U_r^t \bar{d}^{(0)}. \quad (A.18)$$

At this point, there are several ways to proceed which all lead to the same results. The most direct approach is to use the above equations, and write the solutions in eqs. (A.17) and (A.18) as eigenvector expansions, i.e., from (A.17) one finds $$\bar{a}_\gamma = \sum_{i=1}^{r} \frac{Q_i \bar{u}_i}{\lambda_i(\gamma)}, \quad (A.19)$$

where, $$Q_i = \bar{u}_i \cdot \bar{d}, \quad (A.19a)$$

are the projections of the data onto the eigenvectors. Likewise from (A.18), $$\bar{a}^0 = \sum_{i=1}^{r} \frac{Q_i^p \bar{u}_i}{\lambda_i(0)}, \quad (A.20)$$

where $$Q_i^p = \bar{u}_i \cdot \bar{a}^0 \equiv Q_1 - Q_{0,i}. \quad (A.21)$$

In obtaining the above equation, I have used (A.8) and have defined the projections $Q_{0,i} = \bar{u}_i^t \cdot \bar{n}$ of the noise onto the non-null space of $M_0$. The criterion for selecting $\gamma$ is that the squared norm of the difference vector, $a_\gamma - a^0$, be a minimum. Therefore, one is led to the minimization of the function $F_{65}$ where $$F_\gamma = (\bar{a}_\gamma - \bar{a}^0)^t \cdot (\bar{a}_\gamma - \bar{a}), \quad (A.22)$$

where (.) denotes the ordinary scalar product.

Combining eqs. (A.19)–(A.22) and using the orthonormality conditions one finds that $$F_\gamma = \gamma^2 \sum_{i=1}^{r} \frac{Q_i^2}{\lambda_i^2(0)\lambda_i^2(\gamma)} = 2 \sum_{i=1}^{r} \frac{Q_i Q_{0,i}}{\lambda_i(0)\lambda_i(\gamma)} + C_1, \quad (A.23)$$

where $C_1$ is a constant independent of $\gamma$, i.e., $$C_1 = \sum_{i=1}^{r} \frac{Q_{0,i}^2 - 2Q_{0,i}Q_i}{\lambda_i^2(0)}. \quad (A.24)$$

To proceed with the minimization of $F_\gamma$, it is necessary to select a direction for the vector $\bar{Q}_0$. The function is maximized (minimized) with respect to the noise by choosing $\bar{Q}_0$ parallel (anti-parallel) to $\bar{Q}$. A conservative approach, also followed by Butler, Reeds and Dawson[9] is to assume that the vectors are parallel. This assumption is not rigorously justifiable but errs on the side of over smoothing (selecting too large a $\gamma$) which is much less dangerous than under smoothing which can result in a wildly oscillatory and meaningless inverse. Thus one is lead to write, $$\bar{Q}_0 = s\bar{Q}, \quad (A.25),$$

where the scalar s is determined below.

Requiring that the derivative of $F_\gamma$ with respect to $\gamma$ vanish, leads to a trancendental equation whose solution determines $\gamma_{opt}$, i.e., $$\gamma = \bar{s} \frac{N(\gamma)}{D(\gamma)}, \quad (A.26)$$

where, $$N(\gamma) = \sum_{i=1}^{r} \frac{Q_i^2}{\lambda_i^3(\gamma)}, \quad (A.27)$$

and, $$D(\gamma) = \sum_{i=1}^{r} \frac{Q_i^2}{\lambda_i^3(\gamma)\lambda_i(0)}, \quad (A.28)$$

and, $$\bar{s} = \frac{s}{1-s}. \quad (A.29)$$

According to the criterion used in this Appendix, an optimal value of $\gamma$ can be found by finding the non-negative roots of eq. (A.26). The equation is solved numerically, by using Newton's method. Note that, by inspection of (A.26) that for noise free data (i.e., s=0) that $\gamma = 0$ as required. From (A.26) one can prove that the equation always has a unique non-negative solution for s<1 which is bounded in the interval, $$\gamma_l < \gamma_{opt} < \gamma_u, \quad (A.30)$$

where $\gamma_l = \bar{s}\lambda_r(0)$ and $\gamma_u = \bar{s}\lambda_1(0)$.

To complete this Appendix, it remains to determine the scalar s in eq. (A.25). To this end, note that $$\delta = \sqrt{\frac{\bar{Q}_0^t \cdot \bar{Q}_0}{\bar{Q}^t \cdot \bar{Q}}}. \quad (A.31)$$

Using, (A.19a) one finds that, $$\bar{Q}^t \cdot \bar{Q} = \sum_{i,k=1}^{N_c} d_i d_k S_{i,k}, \quad (A.32)$$

where the $d_i$ are the components of the data vector defined in (A.3) and, $$S_{i,k} = \sum_{i=1}^{r} u_i^j u_k^j. \quad (A.33)$$

Similarly, using (A.21) one finds that, $$<\bar{Q}_0^t \cdot \bar{Q}_0> = \sum_{i,k=1}^{N_c} <n_i n_k> S_{i,k}, \quad (A.34)$$

where the $n_i$ are the components of the noise vector defined in (A.9) and where it has been assumed that in computing s one can replace the random variable $Q_0^t \cdot Q_0$ by its expectation value.

Finally, using (A.9) and the statistical properties of the noise one finds that, $$<\bar{Q}_0^t \cdot \bar{Q}_0> = \psi \sum_{m=1}^{N_\omega} \sum_{i,k=1}^{N_c} \frac{S_{i,k} f_i f_k F_{m,m+1}(T_{2,i}) F_{m,m+1}(T_{2,k})}{\delta_{m,m+1}^2} \quad (A.35)$$

Appendix B: Proof that M is Positive Definite

Recall from (A.7) that, $$M_{l,k} = M_{l,k}^{(0)} + \gamma \delta_{l,k}, \quad (B.1)$$

where from (67) and (A.4), $$M_{l,k}^{(0)} = \sum_{m=1}^{N_\omega} \frac{f_k F_{m,m+1}(T_{2,k}) f_l F_{m,m+1}(T_{2,l})}{\delta_{m,m+1}^2}. \quad (B.2)$$

Note that $M_{l,k}^{(0)}$ can be written in the form, $$M_{l,k}^{(0)} = \sum_{m=1}^{N_\omega} B_{l,m}^t B_{m,k} = (B^t \cdot B)_{l,k}, \quad \text{(B.3)}$$

where I have defined the matrix, $$B_{m,k} = \frac{f_k F_{m,m+1}(T_{2,k})}{\partial_{m,m+1}}. \quad \text{(B.4)}$$

For an arbitrary vector $\overline{V} \in R^{N_s \times 1}$, note that $$\overline{V}^t B^t B \overline{V} \equiv \|B\overline{V}\|^2 \geq 0, \quad \text{(B.5)}$$

so that $M^{(0)}$ is positive semi-definite. More specifically, since $\overline{V}$ is arbitrary, one can choose it to be any eigenvector of $M^{(0)}$, e.g., $\overline{u}_j$ from which it follows that $\lambda_j(0) \geq 0$. For $\gamma > 0$, it follows from (A.15) that $\lambda_j(\gamma) > 0$ so that M is positive definite.

Appendix C: Calculation of $\Delta\phi$

Recall from eq. (44) that the free-fluid porosity is defined by, $$\phi_f = K_{tool} \sum_{l=N_c}^{N_c} a_l + \Delta\phi, \quad \text{(C.1)}$$

where $K_{tool}$ is the tool constant.

This Appendix derives the correction $\Delta\phi$ in the above equation. This correction is needed because the bound-fluid porosity cut-off $T_c$ generally does not lie on the leftmost endpoint of the free-fluid porosity integration interval. The correction is in practice almost negligble. It does not affect $\phi_{nmr}$, only its partitioning into free and bound fluid porosity. It can be determined exactly by specifying the closed interval $[T_{min}, T_{max}]$ and the number of integration points $N_s$ which determines a set of logarithmically spaced $T_{2,l}$ values for $l=1,2,\ldots,N_s$. The l-th integration element is a rectangular strip of height $P(T_{2,l})$, width $\delta_l$ and area $a_l \equiv P(T_{2,l}) \delta_l$ where, $$\delta_l = \frac{T_{2,l+1} - T_{2,l-1}}{2}. \quad \text{(C.2)}$$

The integer $N_c$ in (C.1) is defined such that $T_{2,l} \geq T_c$ for $l=N_c,\ldots,N_s$. The endpoints of the rectangular strips are at the midpoints of adjacent values of $T_{2,l}$. For example, let $\tau_l$ denote the midpoint (also the leftmost integration point for the area element $a_l$). Then by definition, $$\eta = \frac{T_{2,l} + T_{2,l-1}}{2}. \quad \text{(C.3)}$$

Note that the widths ($\delta_l$) of the rectangular strips can be written in terms of the $\tau_l$, i.e., $$\delta_l = \tau_{l+1} - \tau_l. \quad \text{(C.4)}$$

Figure 26:
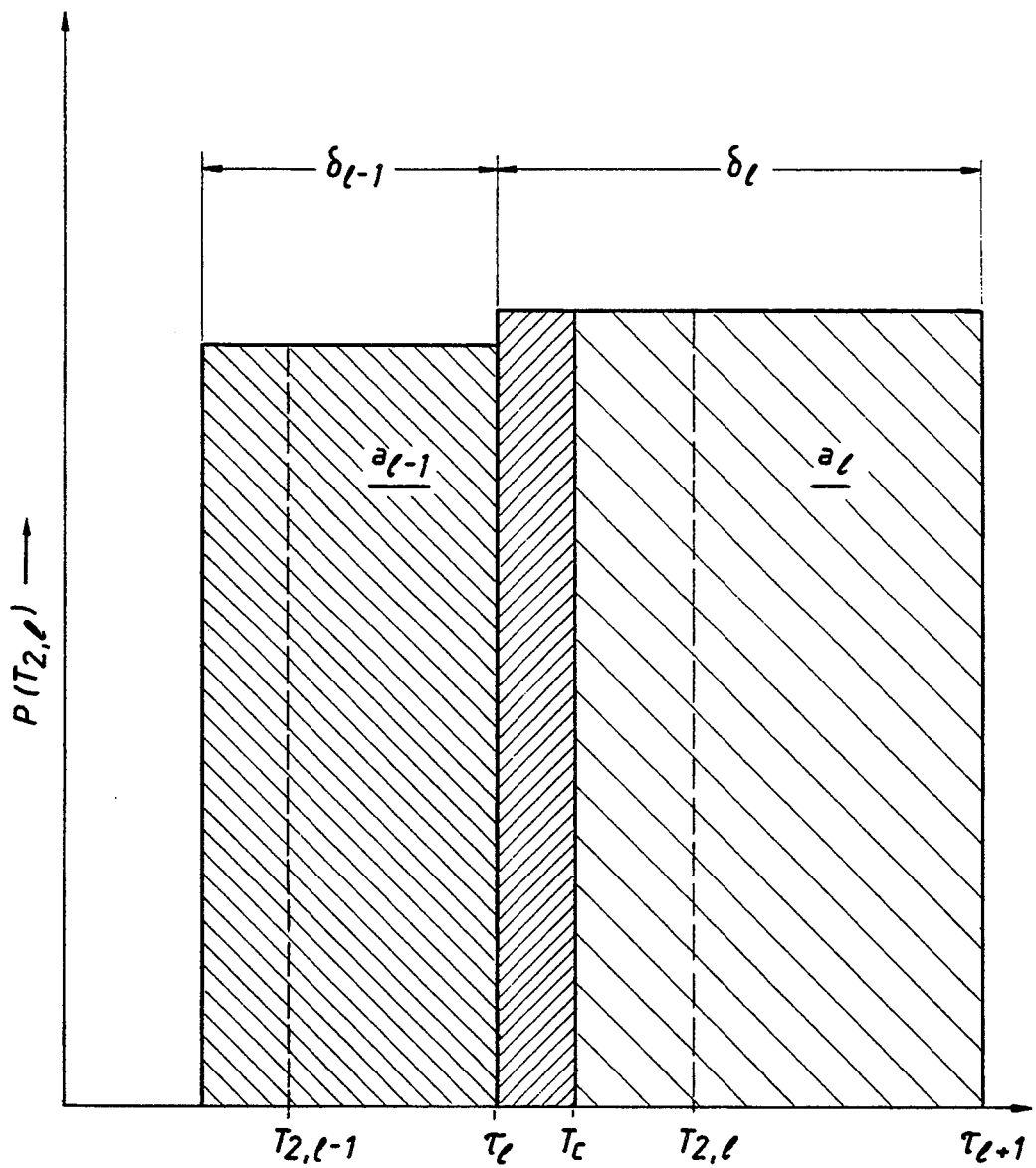
FIG. 26 illustrates a correction "delta phi" used in equation C.1 associated with a calculation of "delta phi".

This above described picture is shown schematically in FIG. 26 for the two rectangular integration elements corresponding to $l=N_c-1$ and $l=N_c$.

In general, there are two cases to consider: (a) $\tau \leq T_c$ or (b) $\tau > T_c$. Case (a) is illustrated in FIG. 26. In case (a), the correction $\Delta\phi \leq 0$, so that the correction subtracts porosity from the summation in (C.1) which includes a small amount of bound fluid porosity. The porosity correction is the sand shaded area in FIG. 26 multiplied by the tool constant. This correction increases the bound fluid porosity by an equal amount.

A simple calculation shows that for case (a):

$$\Delta\phi = -\frac{2K_{tool}(T_c - \tau)a_{N_c}}{T_{2,N_c+1} - T_{2,N_c}}, \quad \text{(C.5)}$$

and for case (b) one finds that, $$\Delta\phi = -\frac{2K_{tool}(\tau - T_c)a_{N_c-1}}{T_{2,N_c} - T_{2,N_c-2}}. \quad \text{(C.6)}$$

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

I claim:

1. A system adapted to be disposed in a wellbore, comprising:
   means for stimulating a porous earth formation traversed by said wellbore;
   means responsive to the stimulation of said formation for receiving a plurality of signals from said formation, said plurality of signals being representative of a set of characteristics relating to physical properties of said formation;
   compression means responsive to said plurality of signals received from said formation for generating a plurality of values expressed in units of volts, said plurality of values generated by said compression means being less in number than said plurality of signals received by said compression means; and
   means for transmitting said plurality of values uphole from said system when said system is disposed in said wellbore to a surface of said wellbore.

2. The system of claim 1, wherein said compression means comprises:
   first means for subdividing said plurality of signals into a plurality of groups,
   said plurality of groups being less in number than said plurality of signals.

3. The system of claim 2, wherein said compression means further comprises:
   second means for generating said plurality of values corresponding, respectively, to said plurality of groups,
   said plurality of values being less in number than said plurality of signals.

4. The system of claim 3, wherein each of said plurality of groups formed by said first means include a subset of said plurality of signals, and wherein said second means comprises:
   summing means for summing said subset of said plurality of signals in each group of said plurality of groups thereby generating said plurality of values corresponding, respectively, to said plurality of groups, one of said values being generated for each group of said plurality of groups.

5. The system of claim 1, wherein said means for receiving receives a plurality of spin echo receiver voltage pulses from said formation and generates a plurality of inphase and quadrature amplitudes from said plurality of spin echo receiver voltage pulses, said means for receiving generating a plurality of signal plus noise amplitudes $A_j(+)$ corresponding, respectively, to said plurality of inphase and quadrature amplitudes, said plurality of signal plus noise amplitudes $A_j(+)$ being said plurality of signals received from said formation.

6. The system of claim 5, wherein said compression means comprises:
  first means for subdividing said plurality of signal plus noise amplitudes $A_j(+)$ into a plurality of groups, where said plurality of groups is less in number than said plurality of signal plus noise amplitudes $A_j(+)$.

7. The system of claim 6, wherein said compression means further comprises:
  second means for generating a value for each of said plurality of groups thereby generating said plurality of values corresponding, respectively, to said plurality of groups.

8. The system of claim 7, wherein each of said plurality of groups formed by said first means include a subset of said plurality of signal plus noise amplitudes $A_j(+)$, and wherein said second means comprises:
  summing means for summing said subset of said plurality of signal plus noise amplitudes $A_j(+)$ in each group of said plurality of groups thereby generating said plurality of values corresponding, respectively, to said plurality of groups, one of said values being generated for each group of said plurality of groups.

9. A method of compressing a first plurality of signals received from a porous earth formation traversed by a wellbore prior to transmitting the compressed signals uphole to a surface apparatus disposed on a surface of said wellbore, said first plurality of signals being generated from said formation in response to a stimulation of said formation and representing a set of characteristics relating to physical properties of said porous earth formation, said first plurality of signals consisting of a first number of signals, comprising the step of:
  (a) reducing said first plurality of signals thereby generating a second plurality of signals consisting of a second number of signals expressed in units of volts and representing said compressed signals, said second number of signals being less in number than said first number of signals,
  said second plurality of signals representing said compressed signals being transmitted uphole following the reducing step.

10. The method of claim 9, wherein the reducing step (a) comprises the step of:
  (b) subdividing said first plurality of signals into a plurality of groups, where said plurality of groups is less in number than said first plurality of signals.

11. The method of claim 10, wherein the reducing step (a) further comprises the step of:
  (c) generating a plurality of values corresponding, respectively, to said plurality of groups,
  said plurality of values being less in number than said first plurality of signals.

12. The method of claim 11, wherein each group of said plurality of groups formed during the subdividing step (b) include a subset of said first plurality of signals, the generating step (c) comprising the step of:
  (d) summing said subset of said first plurality of signals in each group of said plurality of groups thereby generating said plurality of values corresponding, respectively, to said plurality of groups, one of said values being generated for each group of said plurality of groups.

13. The method of claim 9, wherein a plurality of spin echo receiver voltage pulses are received from said formation traversed by said wellbore, a plurality of inphase and quadrature amplitudes result from said spin echo receiver voltage pulses, a plurality of signal plus noise amplitudes $A_j(+)$ result from said plurality of inphase and quadrature amplitudes,
  said first plurality of signals received from said formation and reduced during the reducing step (a) consisting of said plurality of signal plus noise amplitudes $A_j(+)$.

14. The method of claim 13, wherein the reducing step (a) comprises the step of:
  (e) subdividing said plurality of signal plus noise amplitudes $A_j(+)$ into said plurality of groups,
  said plurality of groups being less in number than said plurality of signal plus noise amplitudes $A_j(+)$.

15. The method of claim 14, wherein the reducing step (a) further comprises the step of:
  (f) generating a plurality of values corresponding, respectively, to said plurality of groups,
  said plurality of values being less in number than said plurality of signal plus noise amplitudes $A_j(+)$.

16. The method of claim 15, wherein each of said plurality of groups formed during the subdividing step (e) include a subset of said plurality of signal plus noise amplitudes $A_j(+)$, the generating step (f) comprising the step of:
  (g) summing said subset of said plurality of signal plus noise amplitudes $A_j(+)$ in each group of said plurality of groups thereby generating said plurality of values corresponding, respectively, to said plurality of groups, one of said values being generated for each group of said plurality of groups.

17. A method of logging a well, comprising the steps of:
  stimulating a formation traversed by a wellbore; receiving a plurality of signals from said formation, the plurality of received signals representing a set of characteristics relating to physical properties of said formation;
  compressing said plurality of received signals and generating a plurality of values in response thereto, said plurality of values being expressed in units of volts and being less in number than said plurality of received signals; and
  transmitting said plurality of values uphole to a surface of said wellbore.

18. The method of claim 17, wherein the compressing step comprises the step of:
  subdividing said plurality of received signals into a plurality of groups, where said plurality of groups is less in number than said plurality of received signals.

19. The method of claim 18, wherein the compressing step further comprises the step of:
  generating said plurality of values corresponding, respectively, to said plurality of groups, 20. The method of claim 19, wherein each group of said plurality of groups formed during the subdividing step include a subset of said plurality of signals, the step of generating said plurality of values comprising the step of:
  summing said subset of said plurality of signals in each group of said plurality of groups thereby generating said plurality of values corresponding, respectively, to said plurality of groups.
said plurality of values being equal in number to said plurality of groups but being less in number than said plurality of signals.

21. A system adapted to be disposed in a wellbore, comprising:
means for stimulating a porous earth formation traversed by said wellbore;
means responsive to the stimulation of said formation for receiving a plurality of signals from said formation, said plurality of signals being representative of a set of characteristics relating to physical properties of said formation;
compression means responsive to said plurality of signals received from said formation for generating a plurality of values, said plurality of values being expressed in units of volts,
said plurality of values generated by said compression means being quantitatively less than said plurality of signals received by said compression means from said formation; and
means for transmitting said plurality of values uphole from said system when said system is disposed in said wellbore to a surface of said wellbore.

22. The system of claim 21, wherein said plurality of values generated by said compression means consists of a first number of said values, said plurality of signals received by said compression means consisting of a second number of said signals, said first number of said values generated by said compression means being less than said second number of said signals received by said compression means.

23. The system of claim 22, wherein said compression means comprises:
first means for subdividing said plurality of signals into a plurality of groups,
said plurality of groups being less in number than said plurality of signals.

24. The system of claim 23, wherein said compression means further comprises:
second means for generating said plurality of values corresponding, respectively, to said plurality of groups,
said plurality of values being equal in number to said plurality of groups but being less in number than said plurality of signals.

25. The system of claim 24, wherein each of said plurality of groups formed by said first means include a subset of said plurality of signals, and wherein said second means comprises:
summing means for summing said subset of said plurality of signals in each group of said plurality of groups thereby generating said plurality of values corresponding, respectively, to said plurality of groups, one of said values being generated for each group of said plurality of groups.

26. The system of claim 22, wherein said means for receiving receives a plurality of spin echo receiver voltage pulses from said formation and generates a plurality of inphase and quadrature amplitudes in response to said plurality of spin echo receiver voltage pulses,
said means for receiving generating a plurality of signal plus noise amplitudes $A_j(+)$ corresponding, respectively, to said plurality of inphase and quadrature amplitudes,
said plurality of signals received from said formation consisting of said plurality of signal plus noise amplitudes $A_j(+)$.

27. The system of claim 26, wherein said compression means comprises:
first means for subdividing said plurality of signal plus noise amplitudes $A_j(+)$ into a plurality of groups, where said plurality of groups is less in number than said plurality of signal plus noise amplitudes $A_j(+)$.

28. The system of claim 27, wherein said compression means further comprises:
second means for generating a plurality of values corresponding, respectively, to said plurality of groups.

29. The system of claim 28, wherein each of said plurality of groups formed by said first means include a subset of said plurality of signal plus noise amplitudes $A_j(+)$, and wherein said second means comprises:
summing means for summing said subset of said plurality of signal plus noise amplitudes $A_j(+)$ in each group of said plurality of groups thereby generating said plurality of values corresponding, respectively, to said plurality of groups, one of said values being generated for each group of said plurality of groups.

30. A method of compressing a first plurality of signals received from a porous earth formation traversed by a wellbore prior and transmitting the compressed signals uphole to a surface apparatus disposed on a surface of said wellbore, said first plurality of signals being generated from said formation in response to a stimulation of said formation, comprising the step of:
(a) reducing said first plurality of signals received from said formation and generating a second plurality of signals in response to the reducing step,
said first plurality of signals representing a set of characteristics relating to physical properties of said porous earth formation and consisting of a first number of signals,
said second plurality of signals each being expressed in units of volts, representing said compressed signals, and consisting of a second number of signals,
said second number of signals of said second plurality of signals being less in number than said first number of signals of said first plurality of signals; and
(b) transmitting said second plurality of signals representing said compressed signals uphole following the reducing step.

31. The method of claim 30, wherein the reducing step (a) comprises the step of:
(c) subdividing said first plurality of signals into a plurality of groups, where said plurality of groups is less in number than said first number of signals of said first plurality of signals.

32. The method of claim 31, wherein the reducing step (a) further comprises the step of:
(d) generating said second plurality of signals corresponding, respectively, to said plurality of groups in response to the subdividing step (c),
said second number of signals of said second plurality of signals corresponding, respectively, to said plurality of groups being less in number than said first number of signals of said first plurality of signals.

33. The method of claim 32, wherein each group of said plurality of groups formed during the subdividing step (c) include a subset of said first plurality of signals, the generating step (d) comprising the step of:

(e) summing said subset of said first plurality of signals in each group of said plurality of groups thereby generating said second plurality of signals corresponding, respectively, to said plurality of groups, one of said second plurality of signals being generated for each group of said plurality of groups.

34. The method of claim 30, wherein a plurality of spin echo receiver voltage pulses are received from said formation traversed by said wellbore, a plurality of inphase and quadrature amplitudes result from said spin echo receiver voltage pulses, a plurality of signal plus noise amplitudes $A_j^{(+)}$ result from said plurality of inphase and quadrature amplitudes, said first plurality of signals received from said formation and reduced during the reducing step (a) consisting of said plurality of signal plus noise amplitudes $A_j^{(+)}$.

35. The method of claim 34, wherein the reducing step (a) comprises the step of:
(f) subdividing said plurality of signal plus noise amplitudes $A_j^{(+)}$ into a plurality of groups,
said plurality of groups being less in number than said plurality of signal plus noise amplitudes $A_j^{(+)}$.

36. The method of claim 35, wherein the reducing step (a) further comprises the step of:
(g) generating said second plurality of signals corresponding, respectively, to said plurality of groups,
said second plurality of signals being equal in number to said plurality of groups but being less in number than said plurality of signal plus noise amplitudes $A_j^{(+)}$.

37. The method of claim 36, wherein each of said plurality of groups formed during the subdividing step (f) include a subset of said plurality of signal plus noise amplitudes $A_j^{(+)}$, the generating step (g) comprising the step of:
(h) summing said subset of said plurality of signal plus noise amplitudes $A_j^{(+)}$ in each group of said plurality of groups thereby generating said second plurality of signals corresponding, respectively, to said plurality of groups, one of said second plurality of signals being generated for each group of said plurality of groups.

38. A method of logging a well when a system is disposed in a wellbore, comprising the steps of:
stimulating a formation traversed by said wellbore;
in response to the stimulating step, receiving a plurality of signals into said system from said formation, said plurality of signals consisting of a first number of said signals and representing a set of characteristics relating to physical properties of said formation;
in response to the receiving step, compressing said plurality of signals, the compressing step including the step of generating a plurality of values in response to said plurality of signals, where said plurality of values are each expressed in units of volts, said plurality of values consisting of a second number of said values,
said second number of said values being less than said first number of said signals; and
transmitting said plurality of values uphole from said system to a surface of said wellbore.

39. The method of claim 38, wherein the compressing step comprises the step of:

subdividing said plurality of signals into a plurality of groups, where said plurality of groups is less in number than said plurality of signals.

40. The method of claim 39, wherein the compressing step further comprises the step of:
generating said plurality of values corresponding, respectively, to said plurality of groups,
said plurality of values being equal in number to said plurality of groups but being less in number than said plurality of signals.

41. The method of claim 40, wherein each group of said plurality of groups formed during the subdividing step include a subset of said plurality of signals, the step of generating a plurality of values comprising the step of:
summing said subset of said plurality of signals in each group of said plurality of groups thereby generating said plurality of values corresponding, respectively, to said plurality of groups.

42. A logging tool adapted to be disposed in a wellbore, comprising:
a transmitter adapted for stimulating a formation traversed by said wellbore;
a receiver adapted for receiving a first plurality of signals from said formation in response to the stimulation of said formation by said transmitter, said first plurality of signals representing a set of characteristics relating to physical properties of said formation;
compression means responsive to said first plurality of signals for compressing said first plurality of signals thereby generating a second plurality of signals; and
means for transmitting said second plurality of signals uphole to a surface of said wellbore when said logging tool is disposed in said wellbore.

43. The logging tool of claim 42, wherein said first plurality of signals consist of a first number of signals, said second plurality of signals consisting of a second number of signals, said second number of signals being less than said first number of signals.

44. The logging tool of claims 43, wherein said second plurality of signals are each expressed in units of volts.

45. A system adapted to be disposed in a wellbore, comprising:
a transmitter adapted for stimulating a formation traversed by said wellbore;
a receiver adapted for receiving a first plurality of signals from said formation representative of at least one characteristic relating to a physical property of said formation;
a data compressor adapted for receiving said first plurality of signals from said receiver, compressing said first plurality of signals, and generating a second plurality of signals in response thereto; and
means for transmitting said second plurality of signals uphole to a surface of said wellbore when said system is disposed in said wellbore.

46. The system of claim 45, wherein said second plurality of signals are each expressed in units of volts and consist of a second number of signals,
said first plurality of signals consisting of a first number of signals,
said second number of signals being less than said first number of signals.

47. A method of logging a well, comprising the steps of:

stimulating a formation traversed by a wellbore;
receiving a first plurality of signals from said formation representative of at least one characteristic relating to a physical property of said formation;
compressing said first plurality of signals thereby generating a second plurality of signals; and
transmitting said second plurality of signals uphole to a surface of said wellbore.

48. The method of claim 47, wherein said first plurality of signals consist of a first number of signals, said second plurality of signals consisting of a second number of signals, and wherein the compressing step comprises the step of:
   compressing said first number of signals of said first plurality of signals and generating said second number of signals of said second plurality of signals in response thereto, said second number of signals of said second plurality of signals being less in number than said first number of signals of said first plurality of signals.

49. The method of claims 47, wherein the stimulating step comprises the steps of:
   lowering a well logging tool into said wellbore; and
   using said well logging tool, stimulating said formation traversed by said wellbore.

50. The method of claim 49, wherein the transmitting step comprises the step of:
   transmitting said second plurality of signals uphole from said well logging tool when said well logging tool is disposed in said wellbore to a surface of said wellbore.

51. The method of claim 50, wherein said first plurality of signals consist of a first number of signals, said second plurality of signals consisting of a second number of signals, and wherein the compressing step comprises the step of:
   compressing said first number of signals of said first plurality of signals and generating said second number of signals of said second plurality of signals in response thereto, said second number of signals of said second plurality of signals being less in number than said first number of signals of said first plurality of signals.

* * * * *